US012559452B2

(12) United States Patent
Kroke et al.

(10) Patent No.: US 12,559,452 B2
(45) Date of Patent: Feb. 24, 2026

(54) METHOD FOR THE SYNTHESIS OF ISOCYANATES

(71) Applicant: CYNiO GmbH, Bitterfeld-Wolfen (DE)

(72) Inventors: Edwin Kroke, Halsbrücke (DE); Franziska Gründler, Freiberg (DE); Marcus Herbig, Freiberg (DE); Marlene-Kirstin Baumhardt, Freiberg (DE)

(73) Assignee: CYNIO GmbH, Bitterfeld-Wolfen (DE)

( * ) Notice: Subject to any disclaimer, the term of this patent is extended or adjusted under 35 U.S.C. 154(b) by 549 days.

(21) Appl. No.: 17/914,519

(22) PCT Filed: Mar. 30, 2021

(86) PCT No.: PCT/DE2021/100312
§ 371 (c)(1),
(2) Date: Sep. 26, 2022

(87) PCT Pub. No.: WO2021/228301
PCT Pub. Date: Nov. 18, 2021

(65) Prior Publication Data

US 2023/0140949 A1 May 11, 2023

(30) Foreign Application Priority Data

May 13, 2020 (DE) ..................... 10 2020 113 028.7

(51) Int. Cl.

| | |
|---|---|
| ***C07C 263/04*** | (2006.01) |
| ***C07F 7/08*** | (2006.01) |
| ***C07F 7/10*** | (2006.01) |
| ***C07F 7/12*** | (2006.01) |
| ***C07F 7/18*** | (2006.01) |

(52) U.S. Cl.
CPC .......... *C07C 263/04* (2013.01); *C07F 7/0834* (2013.01); *C07F 7/10* (2013.01); *C07F 7/12* (2013.01); *C07F 7/1804* (2013.01); *C07F 7/1888* (2013.01); *C07F 7/1896* (2013.01); *C07F 7/188* (2013.01)

(58) Field of Classification Search
None
See application file for complete search history.

(56) References Cited

FOREIGN PATENT DOCUMENTS

WO 2021228301 A1 11/2021

OTHER PUBLICATIONS

Office Action issued on Jan. 18, 2021, in corresponding German Application No. 10 2020 113 028. 7, 10 pages.

Lebedev et al., "Organosilicon synthesis of isocyanates: II. Synthesis of aliphatic, carbocyclic, and fatty-aromatic Isocyanates", Russian Journal of General Chemistry, Mar. 1, 2006, vol. 76, No. 3, pp. 469-477.

Kirilin et al., "New aspects of isocyanate synthesis with the use of O-silylurethanes", Mendeleev Communications, 2017, vol. 27, No. 1, pp. 99-100.

Xu et al., "Stoichiometric Reactions of CO2 and Indium-Silylamides and Catalytic Synthesis of Ureas", Angewandte Chemie International Edition, Nov. 6, 2017, vol. 56, No. 45, 81 pages.

Kirilin et al., "The reaction of chloromethylsilanes with amines, hexamethyldisilazanes, and silyicaramates", Russian Chemical Bulletin, Retrieved from Internet: https://link.springer.com/content/pdf/10.1007/BF00703492.pdf, Oct. 1994, vol. 43, No. 10, pp. 1703-1706.

Birkofer et al., "Siliciumorganische Verbindungen: LXI.N-Trimethylsilyl-Carbamidsäure-Trimethylsilylester; Ein neues Silylierungsmittel", Journal of Organometallic Chemistry, 1975, vol. 99, No. 1, pages C1-C4 (with partial English-language summary).

Szalay et al., "Preparation, crystal structure and thermal decomposition study of some trimethylsilyl esters of dicarbamic acids", Journal of Organometallic Chemistry, Mar. 21, 1996, vol. 510, No. 1, pp. 93-102.

(Continued)

*Primary Examiner* — Amy C Bonaparte
(74) *Attorney, Agent, or Firm* — Maier & Maier, PLLC

(57) ABSTRACT

The invention relates to a method for the preparation of isocyanates. Here it is provided that (i) a first organosilicon compound having at least one silicon atom $Si^1$ and a unit of formula G-I bound thereto (formula G-I)

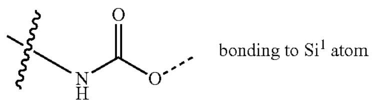

is converted to a third organosilicon compound having a unit of formula G-II (formula G-II)

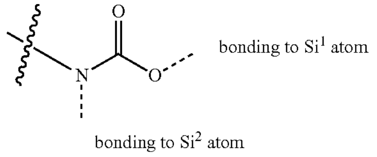

by silylation of the NH group of the unit of formula G-I with a second organosilicon compound having one silicon atom $Si^2$; and (ii) the third organosilicon compound is reacted to an isocyanate by thermolysis, whereby the unit of formula G-II is converted to an isocyanate group.

15 Claims, No Drawings

(56) References Cited

OTHER PUBLICATIONS

Knausz et al., "Trimethylsilylated N- alkyl-substituted carbamates I. preparation and some reactions", Journal of Organometallic Chemistry, 1983, vol. 256, No. 1, pp. 11-21.
Kricheldorf, "Herstellung von N-Silyloxycarbonyl-aminosäure-Derivaten", Synthesis, 1970, vol. 5, 4 pages.
International Search Report issued on Jul. 13, 2021, in corresponding International Application No. PCT/DE2021/100312, 6 pages.
Greber et al., "Eine neue Isocyanat- und Isothiocyanat-Synthese", Angewandte Chemie, 1968, vol. 80, 5 pages.
Wiltzsch et al., "CO2 as an Oxygen Source for Polysiloxanes—Preparation, Crystal Structure and Thermal Decomposition of Two Novel Silylcarbamates", Z. Naturforsch., 2011, vol. 66b, pp. 917-922.
Kraushaar et al., "From CO2 to Polysiloxanes: Di(carbamoyloxy)silanes Me2Si[(OCO)NRR]2 as Precursors for PDMS", Organometallics, 2012, vol. 31, pp. 4779-4785.
Mironov et al., "Siloxycarbonylation of Amines", Zhurnal Obshchei Khimii, 1976, vol. 46, No. 10, pp. 2297-2298.
Fuchter et al., "Clean and efficient synthesis of O-silylcarbamates and ureas in supercritical carbon dioxide", Chemical Communications, 2008, pp. 2152-2154.

METHOD FOR THE SYNTHESIS OF ISOCYANATES

FIELD

The invention relates to a method for the synthesis of isocyanates, in particular of aliphatic and aromatic isocyanates. In particular, it relates to a method for the synthesis of monoisocyanates and for the synthesis of diisocyanates. Furthermore, it relates to the use of compounds for the preparation of an isocyanate.

BACKGROUND

Isocyanates are a very important raw material in numerous industries. Main products prepared from diisocyanates are polyurethanes employed as soft and rigid foams, as components for varnishes and plastic parts, isolations, etc. in many sectors. But also, monoisocyanates are important reactive intermediates, for example to provide urea derivatives or carbamate derivatives for the synthesis of active ingredients, e.g., for pharmaceutical products. In industry, isocyanates are synthesized using phosgene, an extremely toxic and reactive gas. Due to the toxicity, production takes place in cost-intensive, hermetically sealed plants in which the gas is directly utilized after synthesis.

There have been numerous researches on phosgene-free pathways of synthesis of isocyanates, however, none of these methods has been able to establish itself for syntheses on a larger scale. Exemplary reactions are thermal cracking of carbamates and carbamic acid chlorides, transfer of carbonyl groups to amines or decomposition of azides. All of these reactions are accompanied by uneconomic drawbacks, e.g., high temperatures and pressures as well as expensive catalysts. To counteract these drawbacks, applicability of $CO_2$ as a low-cost carbonyl resource has been extensively investigated. However, also these reactions only by using catalysts lead to an acceptable yield.

Formation of isocyanates during cracking of carbamates has been postulated and described in case of N-silylated (i.e., monosilylated) carbamates. Here, silylated carbamates were considered to be particularly promising starting compounds, since the temperature required for cracking can be reduced by silylation (G. Greber, H. R. Kricheldorf, Angew. Chem. 1968, 80, 1028). However, first a carbamic acid chloride, anhydride or ester has to be prepared for the synthesis with comparatively large effort and provided as a starting material for N-silylation. These educts cannot be represented by $CO_2$ insertion into aminosilanes. Here, aminosilanes are meant to be compounds obtained by silylation of a primary amin group to obtain a direct N—Si bond.

Also, O-silylated carbamates which according to the method according to the invention are formed by $CO_2$ insertion into aminosilanes (stage 2 in scheme 9), can be cleaved by thermolysis. However, in the thermal decomposition of these mono-silylated carbamates no isocyanates are formed but the corresponding urea derivatives (a) DE 10 2009 045 849 A1); b) C. Wiltzsch, K. Kraushaar, A. Schwarzer, E. Kroke, Z. *Naturforsch.* 2011, 66b, 917; c) K. Kraushaar, C. Wiltzsch, J. Wagler, U. Böhme, A. Schwarzer, G. Roewer, E. Kroke, *Organometallics* 2012, 31, 4779.).

Knausz et al. in 1983 postulate the formation of an N,O-bissilylated carbamate in the condensed gas phase and its simultaneous decomposition to the isocyanate during cracking of mono-silylated aliphatic carbamates (D. Knausz, A. Meszticzky, L. Szakács, B. Csákvári, K. Újszászy, *J. Organomet. Chem.* 1983, 256, 11). However, the isocyanate could neither be detected nor isolated, since subsequently it immediately reacts with the amine which is also released during the reaction to the corresponding urea derivative.

Further approaches relate to trimethyl-silylated aliphatic dicarbamates which however depend on catalysts and water scavengers (V. F. Mironov, V. D. Sheludyakov, A. D. Kirilin, Zh. *Obshch. Khim.* 1976, 46, 2396) or exclusively yield ureas as product (R. Szalay, Z. Böcskei, D. Knausz, C. Lovász, K. Újszászy, L. Szakács, P. Sohár, *J.* Organomet. Chem. 1996, 510, 93). Fuchter et al. developed a one-step synthesis of urea derivatives using aliphatic aminosilanes and supercritical $CO_2$ (M. J. Fuchter, C. J. Smith, M. W. S. Tsang, A. Boyer, S. Saubern, J. H. Ryan, A. B. Holmes, *Chem. Commun.* (Cambridge, U. K) 2008, 2152). O-Silylcarbamates are formed as isolable intermediates. Considering the research of Knausz (1983) they assume the intermediate formation of isocyanates. Working with supercritical $CO_2$ represents a crucial, economic drawback.

It is therefore desired to find a phosgene-free synthesis pathway permitting an economic preparation of isocyanates. In addition, reduction of cost-intensive parameters is desired. In particular, high yields, low energy consumption and the use of low-cost raw materials are to be achieved.

SUMMARY

The object of the invention is to eliminate the drawbacks according to the prior art. In particular, there is provided a method for the synthesis of isocyanates, in particular of aliphatic and aromatic mono, di and triisocyanates, which permits their economic preparation without using phosgene.

Said object is solved by the features of claims 1 and 15. Suitable developments of the inventions result from the features of the dependent claims.

According to the invention there is provided a method for the preparation of isocyanates, wherein (i) a first organosilicon compound having at least one silicon atom $Si^1$ and a unit of formula G-I bound thereto (formula G-I)

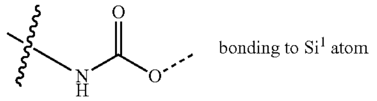

is converted to a third organosilicon compound having a unit of formula G-II (formula G-II)

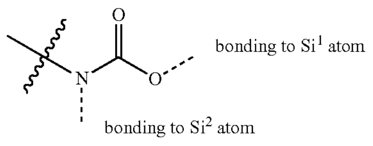

by silylation of the NH group of the unit of formula G-I with a second organosilicon compound having one silicon atom $Si^2$; and (ii) the third organosilicon compound is reacted to an isocyanate by thermolysis, whereby the unit of formula G-II is converted to an isocyanate group.

The method according to the invention permits to prepare isocyanates, in particular aliphatic and aromatic isocyanates, in high yields and of high purity. Here, the isocyanates can be prepared without using phosgene. The method according to the invention therefore permits to safely prepare isocyanates. In addition, the method according to the invention is associated with low energy consumption. It can be carried out at comparatively moderate temperatures. It is not required to use a catalyst. That's why the method according to the invention can be carried out without using a catalyst.

DETAILED DESCRIPTION

The method according to the invention can be used to prepare mono, di and triisocyanates. For the preparation of a diisocyanate the first organosilicon compound has a second silicon atom $Si^1$ to which a second unit of formula G-I is bound. For the preparation of a triisocyanate the first organosilicon compound has a second silicon atom $Si^1$ to which a second unit of formula G-I is bound and a third silicon atom $Si^1$ to which a third unit of formula G-I is bound. The first organosilicon compound can have further silicon atoms $Si^1$ to which one unit of formula G-I is bound each. The number of the silicon atoms $Si^1$ to which one unit of formula G-I is bound each corresponds to the number of the isocyanate groups the isocyanate prepared has. In the unit of formula G-I one hydrogen atom is bound to the nitrogen atom. For the preparation of aliphatic and aromatic isocyanates no further hydrogen atom must be bound to this nitrogen atom. This applies to aliphatic and aromatic isocyanates independent of whether they are substituted or unsubstituted, aliphatic or aromatic isocyanates.

The term "$Si^1$" designates silicon atoms having the first organosilicon compound. The term "$Si^2$" designates the silicon atom having the second organosilicon compound. Exponents "1" and "2" are only for indicating the affiliation of the silicon atoms to the corresponding formulas G-I and G-II. When reacting the first organosilicon compound with the second organosilicon compound the third organosilicon compound is obtained containing both the silicon atoms $Si^1$ derived from the first organosilicon compound and the silicon atoms $Si^2$ derived from the second organosilicon compound.

According to the invention it may be provided that the first organosilicon compound is a compound of general formula II (formula II)

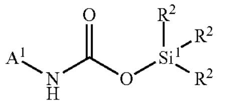

wherein $A^1$ is $R^1$ or a group of general formula G-III:

(formula G-III)

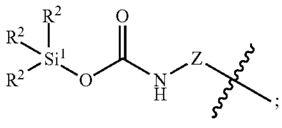

;

$R^1$ is a substituted or unsubstituted, aliphatic or aromatic group;

$R^2$ at each occurrence each independently is selected from the group consisting of hydrogen, a substituted or unsubstituted alkyl group with 1 to 12 carbon atoms and a substituted or unsubstituted aryl group, with the proviso that at least one residue $R^2$ which is not hydrogen is bound to each silicon atom $Si^1$; and Z is a substituted or unsubstituted, aliphatic or aromatic group.

The first organosilicon compound is a O-silylated carbamate. The compound of general formula II is a general example of an O-silylated carbamate. The compound of general formula II is a compound of general formula II-A, if $A^1$ is $R^1$. The compound of general formula II is a compound of general formula II-B, if $A^1$ is a group G-III.

(formula II-A)

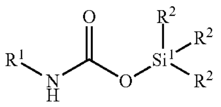

(formula II-B)

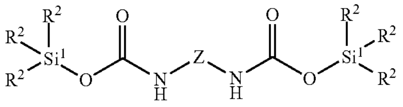

In formula II-A $R^1$ and $R^2$ have the meanings given in connection with formula II. In formula II-B $R^2$ and Z have the meanings given in connection with formula II. Compounds of general formula II-A are suitable for the preparation of monoisocyanates, compounds of general formula II-B are suitable for the preparation of diisocyanates.

$R^1$ preferably is a substituted or unsubstituted, aliphatic group with 1 to 18 carbon atoms or a substituted or unsubstituted aromatic group with 6 to 18 carbon atoms. If $R^1$ is an aliphatic group then it may be provided that it is a branched or unbranched group. $R^1$ may be a substituted or unsubstituted aliphatic group with 1 to 18 carbon atoms or with 1 to 12 carbon atoms.

It may be provided that $R^1$ is selected from the group consisting of a substituted or unsubstituted alkyl group with 1 to 18 carbon atoms, a substituted or unsubstituted heteroalkyl group with 1 to 18 carbon atoms, a substituted or unsubstituted alkenyl group with 1 to 18 carbon atoms, a substituted or unsubstituted alkynyl group with 1 to 18 carbon atoms, a substituted or unsubstituted cycloalkyl group, a substituted or unsubstituted heterocycloalkyl group, a substituted or unsubstituted aryl group, a substituted or unsubstituted heteroaryl group, a substituted or unsubstituted alkylaryl group, and a substituted or unsubstituted arylalkyl group. More preferably, $R^1$ is selected from the group consisting of a substituted or unsubstituted alkyl group with 1 to 12 carbon atoms, a substituted or unsubstituted alkenyl group with 1 to 12 carbon atoms, a substituted or unsubstituted aryl group, a substituted or unsubstituted heteroaryl group, a substituted or unsubstituted alkylaryl group and a substituted or unsubstituted arylalkyl group. If $R^1$ is an alkyl group then $R^1$ for example can be selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted hexyl group, and a substituted or unsubstituted octyl group. If $R^1$ is an alkenyl group then $R^1$ for example may be a substituted or unsubstituted allyl group. If $R^1$ is an aryl group then $R^1$ for example may be a substituted or unsubstituted phenyl group. If $R^1$ is an arylalkyl group then $R^1$ for example may be a substituted or unsubstituted benzyl group. For example, $R^1$ may be selected from the group consisting of n-butyl, n-octyl, allyl, phenyl, and benzyl. In another example $R^1$ is isopentyl.

Preferably, Z is a substituted or unsubstituted, aliphatic group with 1 to 18 carbon atoms or a substituted or unsubstituted aromatic group with 6 to 18 carbon atoms. If Z is an aliphatic group, then it may be provided that it is a branched or unbranched group. Z may be a substituted or unsubstituted aliphatic group with 1 to 18 carbon atoms or with 1 to 12 carbon atoms.

Z is a divalent group unlike $R^1$ which is a monovalent group. It may be provided that Z is a substituted or unsubstituted group having at least one substituted or unsubstituted alkylene group and/or at least one substituted or unsubstituted arylene or heteroarylene group. For example, Z may be selected from a group consisting of a substituted or unsubstituted alkylene group with 1 to 18 carbon atoms, a substituted or unsubstituted phenylene group, and a substituted or unsubstituted phenylene bisalkylene group in which each alkylene group at each occurrence each independently is an alkylene group with 1 to 12 carbon atoms.

It may be provided that at least one residue $R^2$ which is not hydrogen is bound to each silicon atom $Si^1$. As a result, a —$Si^1H_3$ is excluded. Preferably, in the compound of general formula II $R^2$ at each occurrence each independently are a substituted or unsubstituted alkyl group with 1 to 6 carbon atoms. More preferably, in the compound of general formula II $R^2$ at each occurrence each independently are selected from the group consisting of a substituted or unsubstituted methyl group, a substituted or unsubstituted ethyl group, a substituted or unsubstituted propyl group, and a substituted or unsubstituted butyl group. Even more preferably, in the compound of general formula II $R^2$ at each occurrence each independently are selected from the group consisting of an unsubstituted methyl group, an unsubstituted ethyl group, an unsubstituted propyl group, and an unsubstituted butyl group, wherein a methyl group is particularly preferred. In the compound of general formula II $R^2$ at each occurrence may have the same meaning or different meanings. Preferably, all of $R^2$ are a methyl group.

The second organosilicon compound is a silylating agent. According to the invention it may be provided that the second organosilicon compound is a compound of general formula III (formula III)

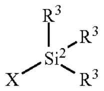

wherein

X is selected from the group consisting of a halogen, —CN, —OCN, —SCN, —$N_3$, a sulphonate, a carbamate, —O—$R^4$, —$NR^7R^8$ and an N-heterocycle;

$R^3$ at each occurrence each independently is selected from the group consisting of hydrogen, a substituted or unsubstituted alkyl group with 1 to 12 carbon atoms and a substituted or unsubstituted aryl group, with the proviso that at least one residue $R^2$ which is not hydrogen is bound to each silicon atom $Si^2$;

$R^4$ is —C(O)$R^9$ or a group of general formula G-VI (formula G-VI)

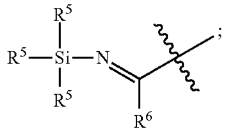

$R^5$ at each occurrence each independently is a substituted or unsubstituted alkyl group with 1 to 12 carbon atoms;

$R^6$ is a substituted or unsubstituted alkyl group with 1 to 12 carbon atoms;

$R^7$ and $R^8$ each independently are a substituted or unsubstituted alkyl group with 1 to 12 carbon atoms or —C(O)$R^9$; and $R^9$ is a substituted or unsubstituted alkyl group with 1 to 12 carbon atoms.

However, other silylating agents may also be used. Examples of other silylating agents comprise without being limited thereto aminosilanes permitting transamination or transsilylation and silazanes. See, for example P. L. Fuchs (ed.) *Handbook of reagents for organic synthesis*, John Wiley & Sons Inc, London, 2011. Further examples of suitable silylating agents are given in table 1.

The second organosilicon compound bears a leaving group X. It is a silylating agent. The compound of general formula III is a general example of such a silane.

X may be selected from the group consisting of a halogen, a sulphonate, a carbamate, —O—$R^4$, —$NR^7R^8$, and an N-heterocycle. It may be provided that X is a sulphonate. The term "sulphonate" is meant to be an $R^S$—$SO_2$—O group. $R^S$ may be for example a branched or unbranched, substituted or unsubstituted $C_1$-$C_6$-alkyl group, a substituted or unsubstituted aryl group, a substituted or unsubstituted alkylaryl group, or a substituted or unsubstituted silane group. Preferably, $R^S$ is $CH_3$—, $CF_3$—, $CH_3$—$C_6H_4$—, or —O—$Si(CH_3)_3$. The sulphonate may be for example selected from the group consisting of a toluene sulphonic acid ester group, a methyl sulphonic acid ester group, and a trifluoromethyl sulphonic acid ester group. A toluene sulphonic acid ester group is meant to be a —OTs group, wherein Ts is tosyl. A methyl sulphonic acid ester group is meant to be a —OMs group, wherein Ms is mesyl. A trifluoromethyl sulphonic acid ester group is meant to be a $CF_3$—$SO_2$—O—. A trifluoromethyl sulphonic acid ester group is also referred to as triflate.

It may be provided that X is a carbamate. The term "carbamate" is meant to be a $(R^N)_2$N—CO—O group. $R^N$ may be for example a branched or unbranched, substituted or unsubstituted $C_1$-$C_6$ alkyl group, a substituted or unsubstituted aryl group, or a substituted or unsubstituted alkylaryl group. Preferably, $R^N$ is $CH_3$— or $CH_3$—$CH_2$—. An example of a compound of general formula III in which X is a carbamate is $(CH_3)_3Si$—O—CO—$N(CH_3)_2$.

It may be provided that X is —$NR^7R^8$. In one variant $R^7$ and $R^8$ each independently are a substituted or unsubstituted alkyl group with 1 to 6 carbon atoms, for example methyl or ethyl. In another variant $R^7$ is a substituted or unsubstituted alkyl group with 1 to 6 carbon atoms and $R^8$ is —C(O)$R^9$, wherein $R^9$ preferably is a substituted or unsubstituted alkyl group with 1 to 6 carbon atoms. For example, $R^7$ is methyl and $R^8$ is —$COCF_3$, —$COCH_3$, or —$COCF_2CF_2CF_3$.

It may be provided that X is an N-heterocycle. The term "N-heterocycle" describes a heterocycloalkyl group, as defined herein, or a heteroaryl group, as defined herein, each with the proviso that at least one of the heteroatoms is nitrogen.

In the compound of general formula III X is preferably selected from the group consisting of chlorine, a toluene sulphonic acid ester group, a methyl sulphonic acid ester group, and a trifluoromethyl sulphonic acid ester group. Preferably, X is a trifluoromethyl sulphonic acid ester group (triflate).

It may be provided that at least one residue $R^2$ which is not hydrogen is bound to each silicon atom $Si^2$. As a result, an $X—Si^2H_3$ is excluded. Preferably, in the compound of general formula III $R^3$ at each occurrence each independently is a substituted or unsubstituted alkyl group with 1 to 6 carbon atoms or phenyl. More preferably, in the compound of general formula III $R^3$ at each occurrence each independently is selected from the group consisting of a substituted or unsubstituted methyl group, a substituted or unsubstituted ethyl group, a substituted or unsubstituted propyl group, and a substituted or unsubstituted phenyl group. Even more preferably, in the compound of general formula III $R^3$ at each occurrence each independently is selected from the group consisting of an unsubstituted methyl group, an unsubstituted ethyl group, an unsubstituted propyl group, and an unsubstituted phenyl group with a methyl group being particularly preferred. In the compound of general formula III $R^3$ at each occurrence may have the same meaning or different meanings. Preferably, all of $R^3$ are a methyl group. A particularly preferred compound of general formula III is trimethylsilyl trifluoromethane sulphonate which is also referred to as trimethylsilyltriflate.

If X is —O—$R^4$ and $R^4$ is a group of general formula G-VI then it may be provided that $R^5$ at each occurrence each independently is an unsubstituted alkyl group with 1 to 6 carbon atoms and that $R^6$ is a fluorinated or unsubstituted alkyl group with 1 to 6 carbon atoms. For example, all of $R^5$ and $R^6$ each may be a methyl group. In this case, the silylating agent is N,O-bis(trimethylsilyl)acetamide (BSA).

If X is —O—$R^4$ and $R^4$ is —C(O)$R^9$ then it may be provided that $R^9$ is a substituted or unsubstituted alkyl group with 1 to 6 carbon atoms. One example of such a compound of general formula III is $(CH_3)_3Si—O—CO—CCl_3$.

Table 1 shows further examples of suitable silylating agents.

TABLE 1

| No. | Formula | Name (Abbreviation) |
|---|---|---|
| S1 | 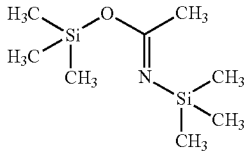 | N,O-bis(trimethylsilyl)-acetamide (BSA) |
| S2 | 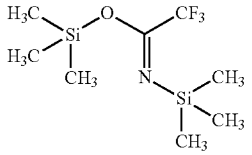 | N,O-bis(trimethylsilyl)-trifluoroacetamide (BSTFA) |
| S3 | 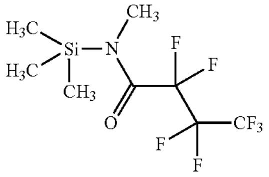 [SMILES: CN(C(=O)C(F)(F)C(F)(F)C(F)(F)F)[Si](C)(C)C] | N-methyl-N-trimethylsilylheptafluorobutyramide (MSHFBA) |
| S4 | 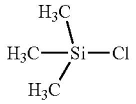 | trimethylchlorosilane (TMCS) |
| S5 | 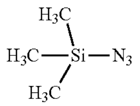 | trimethylsilylazide (TMSA) |
| S6 | 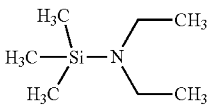 | N-(trimethylsilyl)diethylamine (TMSDEA) |
| S7 | 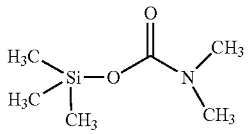 | trimethylsilyl-N,N-dimethylcarbamate (DMCTMS) |

TABLE 1-continued

| No. | Formula | Name (Abbreviation) |
|---|---|---|
| S8 | 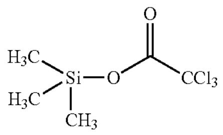 | trimethylsilyltrichloroacetate (TMSTCA) |
| S9 | 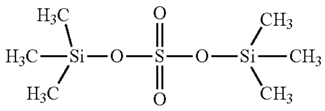 | O, O'-bis(trimethylsilyl)sulphate (BSS) |
| S10 | 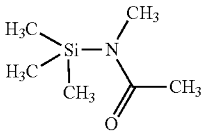 | N-methyl-N-trimethylsilyl-acetamide (MSA) |
| S11 | 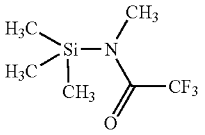 | N-methyl-N-trimethylsilyl-trifluoroacetamide (MSTFA) |
| S12 | 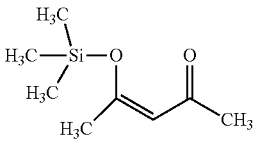 | 4-trimethylsiloxy-3-pentene-2-one (TMSacac) |
| S13 | 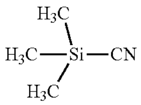 | trimethylsilylcyanide (TMSCN) |
| S14 | 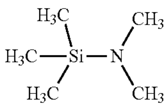 | N-(trimethylsilyl)-dimethylamine (TMSDMA) |
| S15 | 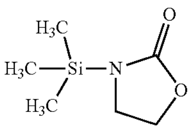 | 3-trimethylsilyl-2-oxazolidinone (TMSO) |
| S16 | 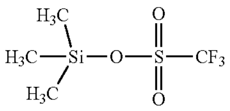 | trimethylsilyltriflate (TMSTF) |

It may be provided that the third organosilicon compound is a compound of general formula IV (formula IV)

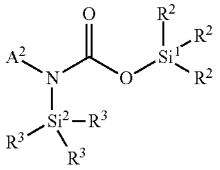

wherein $A^2$ is $R^1$ or a group of general formula G-IV:

(formula G-IV)

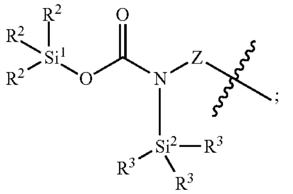

$R^1$, $R^2$, $R^3$ and Z have the meanings given in connection with the compound of general formula II; and $R^3$ at each occurrence has the meanings given in connection with the compound of general formula III.

The compound of general formula IV-A is a compound of general formula IV, if $A^2$ is $R^1$. The compound of general formula IV-B is a compound of general formula IV, if A is a group G-IV.

(formula IV-A)

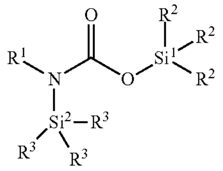

(formula IV-B)

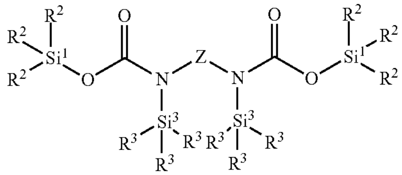

In formula IV-A $R^1$, $R^2$, and $R^3$ have the meanings given in connection with formula II. In formula IV-B $R^2$, $R^3$, and Z have the meanings given in connection with formula II. In formulae IV-A and IV-B $R^3$ at each occurrence have the meanings given in connection with the compound of formula III.

A compound of general formula IV-A is an N,O-bissilylated carbamate. Such a compound is particularly suitable for the preparation of monoisocyanates. Examples of an N,O-bissilylated carbamate are N,O-bis(trimethylsilyl)-N-phenyl-carbamate (1), N,O-bis(trimethylsilyl)-N,n-octyl-carbamate (2), and N,O-bis(trimethylsilyl)-N-benzyl-carbamate (5). A compound of general formula IV-B has two N,O-bissilylated carbamate groups. Such a compound is particularly suitable for the preparation of diisocyanates. Examples of a compound having two N,O-bissilylated carbamate groups are p-[N,N',O,O'-tetrakis(trimethylsilyl)-carbamato]-benzene (3), m-[N,N',O,O'-tetrakis(trimethylsilyl)-carbamato]-xylene (4), and 1,8-[N,N',O,O'-tetrakis(trimethylsilyl)-carbamato]-octane (6). The mentioned compounds are shown in table 2:

TABLE 2

| No. | Formula | Name |
|---|---|---|
| 1 | 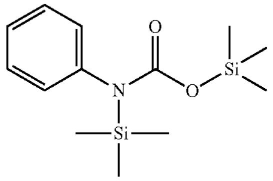 [SMILES: C[Si](C)(C)OC(=O)N(c1ccccc1)[Si](C)(C)C] | N,O-bis(trimethylsilyl)-N-phenyl-carbamate ($R^1$ = phenyl) |
| 2 | 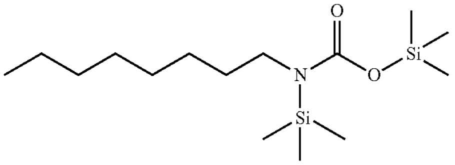 [SMILES: CCCCCCCCN(C(=O)O[Si](C)(C)C)[Si](C)(C)C] | N,O-bis(trimethylsilyl)-N,n-octyl-carbamate ($R^1$ = n-octyl) |
| 3 | 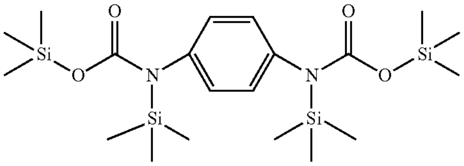 | p-[N,N',O,O'-tetrakis(trimethylsilyl)-carbamato]-benzene (Z = p-phenylene) |

TABLE 2-continued

| No. | Formula | Name |
|---|---|---|
| 4 | 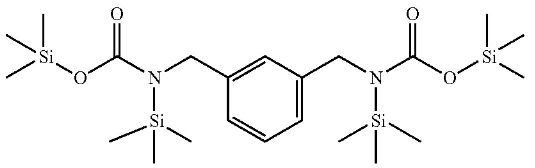 | m-[N,N',O,O'-tetrakis(trimethylsilyl)-carbamato]-xylene (Z = m-xylylene) |
| 5 | 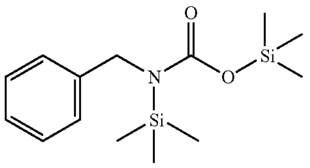 [SMILES: C[Si](C)(C)OC(=O)N(Cc1ccccc1)[Si](C)(C)C] | N,O-bis(trimethylsilyl)-N-benzyl-carbamate ($R^1$ = benzyl) |
| 6 | 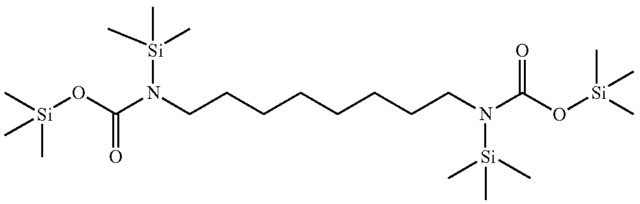 | 1,8-[N,N',O,O'-tetrakis(trimethylsilyl)-carbamato]-octane (Z = $-(CH_2)_8-$) |

The compound of general formula IV may be obtained by reacting the compound of general formula II with the compound of general formula III. Said reaction is a silylation. By means of the silylation a second silyl group is inserted into a carbamate group. The second silyl group is bound to the nitrogen atom of the carbamate group, while the first silyl group is bound to an oxygen atom of the carbamate group. The compound of general formula IV-A may be obtained by reacting the compound of general formula II-A with the compound of general formula III. The compound of general formula IV-B may be obtained by reacting the compound of general formula II-B with the compound of general formula III.

With the method according to the invention isocyanates can be prepared. In the present invention isocyanates are also referred to as isocyanate compounds. An isocyanate may be a compound of general formula I $A^3$-N═C═O (formula I)

wherein $A^3$ is $R^1$ or a group of formula G-V:

O═C═N—Z-§- (formula G-V), $R^1$ and Z have the meanings given in connection with the compound of general formula II.

The compound of general formula I is a compound of general formula I-A, if $A^3$ is $R^1$. The compound of general formula I is a compound of general formula I-B, if $A^3$ is a group G-V.

$R^1$—N═C═O (formula I-A)

O═C═N—Z—N═C═O (formula I-B)

In formula I-A $R^1$ has the meanings given in connection with formula II. If $R^1$ is octyl then the compound of general formula I is octyl isocyanate, if $R^1$ is phenyl then the compound of general formula I is phenyl isocyanate, if $R^1$ is benzyl then the compound of general formula I is benzyl isocyanate. In formula I-B Z has the meanings given in connection with formula II. If Z is phenylene then the compound of general formula I is a diisocyanatobenzene, for example a 1,4-diisocyanatobenzene. If Z is xylylene then the compound of general formula I is a diisocyanatoxylylene, for example a 1,3-xylylene diisocyanate (abbr. mXDI).

The compound of general formula IV may be converted to the compound of general formula I by thermolysis. In particular, a compound of general formula IV-A can be reacted to the compound of general formula I-A by thermolysis. A compound of general formula IV-B can be reacted to the compound of general formula I-B by thermolysis.

Scheme 1 illustrates the preparation of an isocyanate by silylation of the first organosilicon compound having a unit G-I to obtain the third organosilicon compound having a unit G-II and the subsequent reaction of the third organosilicon compound to an isocyanate.

Scheme 1

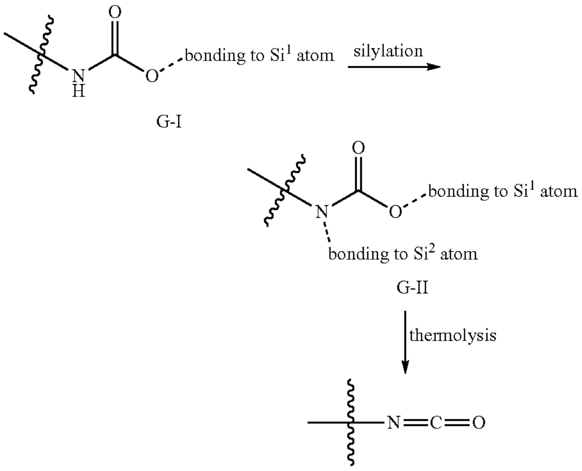

The silylation is carried out by reacting the first organosilicon compound with the second organosilicon compound.

The described silylation for example is particularly suitable for the silylation of aromatic O-trimethyl-silylated carbamates whereby aromatic N,O-bistrimethyl-silylated carbamates are obtained. However, the silylation is also suitable for the silylation for example of aliphatic O-trimethyl-silylated carbamates whereby aliphatic N,O-bistrimethyl-silylated carbamates are obtained.

Scheme 2 illustrates the preparation of an isocyanate of general formula I. For that, silylation of a compound of general formula II with a compound of general formula III is carried out to obtain a compound of general formula IV. Subsequently, the compound of general formula IV is subjected to thermolysis to obtain the isocyanate of general formula I.

Scheme 2

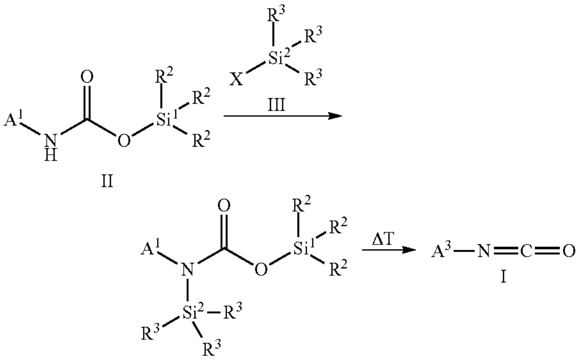

II

IV

I

"ΔT" represents the use of an elevated temperature in the thermolysis.

Schema 3 illustrates the preparation of an isocyanate of general formula I-A. For that, silylation of a compound of general formula II-A with a compound of general formula III is carried out to obtain a compound of general formula IV-A. Subsequently, the compound of general formula IV-A is subjected to thermolysis to obtain the isocyanate of general formula I-A.

Scheme 3

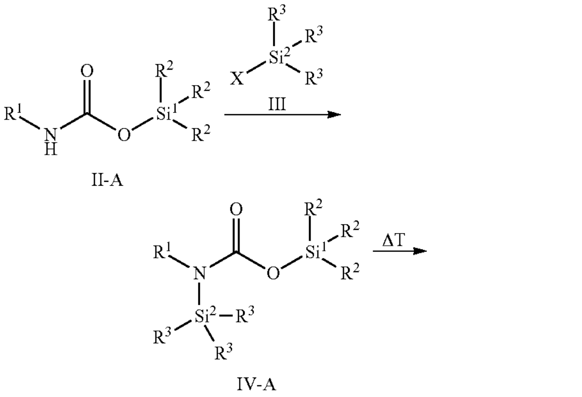

II-A

IV-A

I-A

Schema 4 illustrates the preparation of an isocyanate of general formula I-B. For that, silylation of a compound of general formula II-B with a compound of general formula III is carried out to obtain a compound of general formula IV-B. Subsequently, the compound of general formula IV-B is subjected to thermolysis to obtain the isocyanate of general formula I-B.

Scheme 4

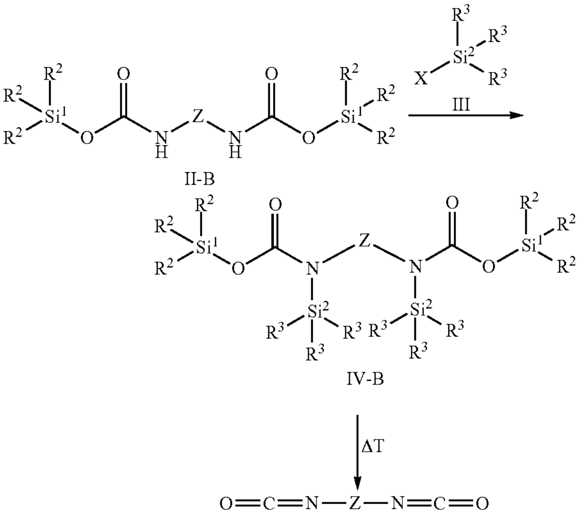

II-B

IV-B

I-B

Silylation of the first organosilicon compound, in particular the compound of general formula II, is preferably carried out in the presence of an auxiliary base. The auxiliary base is for binding the leaving group cleaved-off from the second organosilicon compound, i.e., the silylating agent, in silylation as well as the hydrogen atom which is cleaved-off from the NH group of the compound of general formula II. Said group is the group X in the compound of general formula III. The auxiliary base is preferably an amine, for example a trialkylamine, such as triethylamine, or aniline. A preferred auxiliary base is a triethylamine. It may be provided that an auxiliary base the aliphatic or aromatic residue of which corresponds to the aliphatic or aromatic residue, respectively of the compound of general formula I is used for the preparation of a compound of general formula I. For example, a compound of general formula VI-A can be used as the auxiliary base for the preparation of a compound of general formula I-A. Thus, for the preparation of benzylisocyanate benzylamine is a suitable auxiliary base, for the preparation of phenylisocyanate it is aniline. If no auxiliary base is used there may be the danger that the leaving group forms a reactive acid which has a negative effect on the formation of the third organosilicon compound, in particular of the compound of general formula IV. If the silylating agent is trimethyl chlorosilane and the auxiliary base is triethylamine triethylamine hydrochloride $((CH_3CH_2)_3N*HCl)$ is formed in the silylation.

Silylation is preferably carried out in an aprotic organic solvent. Particularly, preferred are non-polar solvents. Examples of suitable solvents are n-pentane, n-hexane, and anisole with n-pentane being particularly preferred.

Preferably, the first organosilicon compound and the second organosilicon compound are used in a molar ratio such that for each carbamate unit of formula G-I of the first organosilicon compound there is at least one molecule of the second organosilicon compound. It may be provided that the molar ratio of the first organosilicon compound to the second organosilicon compound is 1:n x (1 to 1.5), particularly preferred 1:n x (1 to 1.2), wherein n is the number of the carbamate units of formula G-I. If a monoisocyanate is to be prepared then the first organosilicon compound has a carbamate unit of formula G-I so that n is equal to 1. If a diisocyanate is to be prepared then the first organosilicon compound has two carbamate units of formula G-I so that n is equal to 2. If a triisocyanate is to be prepared then the first organosilicon compound has three carbamate units of formula G-I so that n is equal to 3. It is preferred that the second organosilicon compound is present in a slight excess with respect to the number of the carbamate units of the first organosilicon compound. If an auxiliary base is used then the second organosilicon compound and the auxiliary base can be used in a molar ratio from 1:1 to 1.5, preferably from 1:1 to 1.2.

Silylation is preferably carried out at a temperature between 0 and 50° C., more preferably at 0 to 25° C. and particularly preferred at room temperature. Room temperature is meant to be a temperature between 15 and 25° C. Silylation is preferably carried out under ambient pressure. It may be carried out under an inert gas atmosphere, wherein as the inert gas nitrogen or argon may be used, for example.

Thermolysis is a method for thermal cracking. Thermolysis is preferably carried out at a temperature from 100 to 400° C., more preferably at a temperature from 150 to 350° C. and especially preferred at a temperature of 230 to 300° C. The temperature should not exceed 400° C. in order to prevent a reaction of isocyanates between each other to form di, tri, or oligomers. Preferably, thermolysis is carried out without using a solvent. Preferably, thermolysis is carried out under ambient pressure. It may be carried out under an inert gas atmosphere, wherein for example nitrogen or argon can be used as the inert gas.

Thermolysis can be carried out using a temperature profile. The temperature profile can comprise two or more temperature stages, wherein each temperature stage is applied for a given period of time. Each of the applied temperature stages can be above the previously applied temperature range by 20 to 80° C., for example by 30 to 50° C. The given period of time can be between 1 min and 2 hrs.

The method according to the invention provides the use of the first organosilicon compound having a unit G-I, for example a compound of general formula II. Said first organosilicon compound can be prepared by inserting carbon dioxide into an aminosilane. Here, an aminosilane is meant to be a compound obtained by silylating a primary amine group to obtain a direct N—Si bond. Scheme 5 illustrates the preparation of a compound of general formula II-A by inserting carbon dioxide into an aminosilane of general formula V-A.

Scheme 5

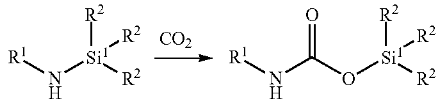

V-A II-A

In the compound of general formula V-A $R^1$ and $R^2$ have the meanings given in connection with general formula II. Scheme 6 illustrates the preparation of a compound of general formula II-B by inserting carbon dioxide into an aminosilane of general formula V-B.

Scheme 6

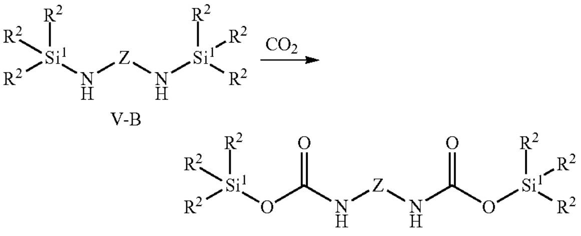

V-B

II-B

The aminosilane of general formula V-B is a compound obtained by silylating two terminal, primary amin groups of a molecule to obtain two direct N—Si bonds. It may be regarded as a double-mono-silylated primary diamine. In the compound of general formula V-B $R^2$ and Z have the meanings given in connection with general formula II.

Insertion of carbon dioxide can be effected by passing in gaseous carbon dioxide into the aminosilane or a solution of the aminosilane in a solvent. Preferably, the solvent is an aprotic organic solvent, for example tetrahydrofuran, diethyl ether, toluene, n-pentane, or n-hexane, with tetrahydrofuran being especially preferred. Insertion can be carried out under ambient pressure or under excess pressure. Using an excess pressure is particularly suitably, if $R^1$ is a substituted or unsubstituted aromatic group or if Z is a substituted or unsubstituted aromatic group. Preferably, the excess pressure is between 1.5 and 10 bar. Insertion can be carried out under an inert gas atmosphere, wherein for example nitrogen or argon can be used as the inert gas. Further details on the insertion of carbon dioxide into an aminosilane are found for example in DE 10 2009 045 849 A1.

Aminosilanes, in particular the aminosilanes of general formula V-A and V-B, can be prepared from substituted or unsubstituted, aliphatic or aromatic primary amines by silylating the amine group with a silylating agent. As the silylating agent the second organosilicon compound, for example the compound of general formula III, or other silylating agents may be used. Scheme 7 shows the preparation of an aminosilane of general formula V-A by silylating a primary amine of general formula VI-A.

Scheme 7

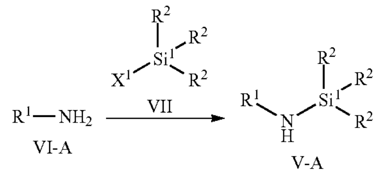

VI-A V-A

In the compound of general formula VI-A $R^1$ has the meanings given in connection with general formula II. The compound of general formula VII is an example of a silylating agent. In the compound of general formula VII $X^1$ is selected from the group consisting of a halogen, —CN, —OCN, —SCN, —$N_3$, a sulphonate and a group —O—$R^4$;

$R^2$ at each occurrence has the meanings given in connection with general formula II;

$R^4$ at each occurrence and $R^5$ have the meanings given in connection with general formula III. Other silylating agents may also be used. Examples of other silylating agents without being limited thereto comprise aminosilanes which enable transamination or transsilylation and silazanes. Further examples of suitable silylating agents are given in table 1.

The compound of general formula VII is a silane bearing a leaving group $X^1$. For silylating the primary amine, a milder silylating agent can be chosen compared to the silylation with the compound of general formula III. A silylating agent is regarded as being milder if it is less reactive. Using a milder silylating agents is possible because a hydrogen atom of a primary amin group is easier to silylate than the hydrogen atom of a carbamate group.

Preferably, $X^1$ is selected from the group consisting of a halogen, a sulphonate, and a group —O—$R^4$. It may be provided that $X^1$ is a sulphonate, i.e., an $R^S$—$SO_2$—O group. For example, $R^S$ may be a branched or unbranched, substituted or unsubstituted $C_1$-$C_6$-alkyl group, an aryl group, or an alkylaryl group. Preferably, $R^S$ is $CH_3$—, $CF_3$—, or $CH_3$—$C_6H_4$—. For example, the sulphonate can be selected from the group consisting of a toluene sulphonic acid ester group, a methyl sulphonic acid ester group and a trifluoromethyl sulphonic acid ester group. In the compound of general formula VII $X^1$ is preferably selected from the group consisting of chlorine, a toluene sulphonic acid ester group, a methyl sulphonic acid ester group and a trifluoromethyl sulphonic acid ester group. Preferably, $X^1$ is chlorine.

Preferably in the compound of general formula VII $R^2$ at each occurrence is an unsubstituted alkyl group with 1 to 6 carbon atoms and $X^1$ is chlorine. In this case, the compound of general formula VII is a trialkyl chlorosilane. A particularly preferred compound of general formula VII is trimethyl chlorosilane. This is an inexpensive silylating agent.

If the primary amine has further primary amino groups, then said amino groups are also silylated. Scheme 8 shows the preparation of an aminosilane of general formula V-B by silylating a primary amine of general formula VI-B. Compound V-B is an amine having two primary amino groups.

Scheme 8

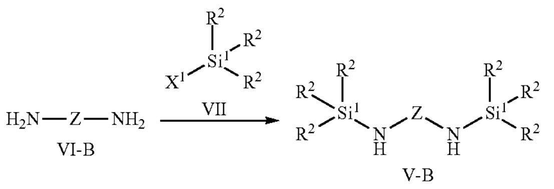

In the compound of general formula VI-B Z has the meanings given in connection with general formula II. The compound of general formula VII has been described above in connection with scheme 7.

The silylation of the primary amine, for example of the primary amine of general formula VI-A or VI-B, preferably is carried out in the presence of an auxiliary base. The auxiliary base is for binding the leaving group cleaved off from the silylating agent during silylation, e.g., the compound of general formula VII, as well as the hydrogen atom cleaved off from the NH group of the compound of general formula II. Said group is the group $X^1$ in the compound of general formula VII. Preferably, the auxiliary base is an amine, for example a trialkyl amine, such as triethyl amine, or aniline. A preferred auxiliary base is a triethyl amine. It may be provided that for the preparation of a compound of general formula I an auxiliary base is used the aliphatic or aromatic residue of which corresponds to the aliphatic or aromatic residue, respectively of the compound of general formula I. For example, for the preparation of a compound of general formula I-A a compound of general formula VI-A can be used as the auxiliary base. Thus, for the preparation of benzyl isocyanate benzyl amine is a suitable auxiliary base, for the preparation of phenyl isocyanate it is aniline. Then, the compound of general formula VI-A or VI-B not only is a starting material, but also the auxiliary base. It is therefore suitable to use the compound of general formula VI-A or VI-B in an excess to the silylating agent, for example in a molar ratio of 2:1. If for 1 molecule of the trimethyl chlorosilane silylating agent 1 molecule of a compound of general formula VI-A or VI-B is used, then HCl is formed which in turn is trapped by a second molecule of the compound of general formula VI-A or VI-B, respectively. Thus, 1 molecule of trimethyl chlorosilane consumes 2 molecules of the compound of general formula VI-A or VI-B, respectively. Without using an auxiliary base there may be the risk that the leaving group forms a reactive acid which has a negative effect on the formation of an aminosilane, e.g., the compound of general formula V-A or V-B. When using a trialkyl chlorosilane as the silylating agent hydrogen chloride is formed during silylation which is trapped with the auxiliary base. If the silylating agent is trimethyl chlorosilane and the auxiliary base is triethyl amine, then triethyl amine hydrochloride (($(CH_3CH_2)_3$ N*HCl) is formed during silylation.

Silylation of the primary amine, for example of the primary amine of general formula VI-A or VI-B can be made under the conditions described above in connection with the silylation of the first organic compound, for example the compound of general formula II. Preferably, silylation of the primary amine is carried out at room temperature and ambient pressure. A catalyst is not required. The aminosilanes are obtained in high yields.

The method according to the invention may be a two-stage method. In this case, the preparation of an isocyanate compound starts with the first organosilicon compound (e.g., a compound of general formula II). The two-stage method provides the silylation of the first organosilicon compound to obtain the third organosilicon compound (in the case of a compound of general formula II this is a compound of general formula IV) and the subsequent thermolysis of the third organosilicon compound to the isocyanate compound (in the case of compound of general formula IV this is a compound of general formula I). The two-stage method can be carried out at ambient pressure. Ambient pressure may mean to be atmospheric pressure. The two-stage method can be carried out under an inert gas atmosphere.

However, if the preparation of an isocyanate compound starts with a primary amine, then the method according to the invention is a four-stage method. The four-stage method provides the silylation of a primary amine to obtain an aminosilane ($1^{st}$ stage), insertion of carbon dioxide into the aminosilane to obtain the first organosilicon compound (e.g., a compound of general formula II) ($2^{nd}$ stage), silylation of the first organosilicon compound to obtain the third organosilicon compound (in the case of a compound of general formula II this is a compound of general formula IV) ($3^{rd}$ stage) and the subsequent thermolysis of the third organosilicon compound to the isocyanate compound (in the case of a compound of general formula IV this is a compound of general formula I) ($4^{th}$ stage). Scheme 9 illustrates the preparation of an isocyanate compound by means of the four-stage method.

Scheme 9

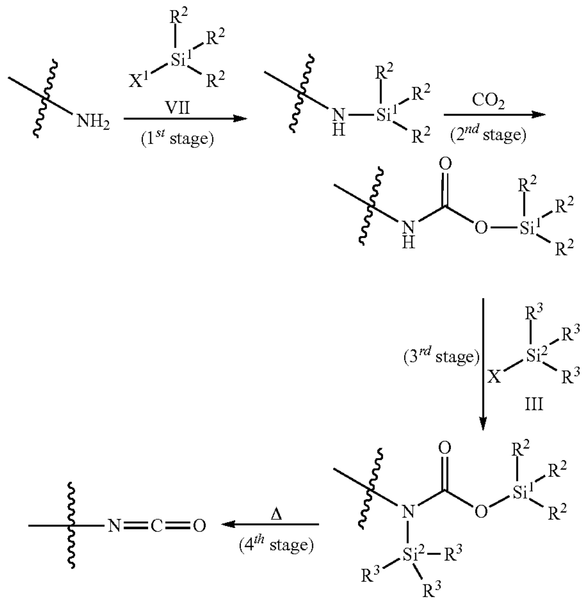

The four-stage synthesis of isocyanates, for example of mono and diisocyanates, comprises the synthesis of aminosilanes from primary amines and a silylating agent such as e.g., trialkyl chlorosilane (stage 1), the reaction of the aminosilanes with $CO_2$ to O-silylated carbamates (stage 2), followed by a second silylation step (stage 3) to obtain N,O-bis-silylated carbamates and the final thermolysis of the bis-silylated $CO_2$ insertion products, i.e., the N,O-bissilylated carbamates (stage 4). The four-stage method refrains from phosgene, relies on $CO_2$ as a carbon and oxygen source and runs without catalyst at moderate temperatures. Also, the two first stages (stages 1 and 2) are characterized by the advantages of all methods according to the invention, such as among others good yields, low reaction heat, etc. All four stages may be carried out under ambient pressure. Ambient pressure can mean atmospheric pressure. The two-stage method can be carried out under an inert gas atmosphere. Using super critical $CO_2$ is not provided.

It is a particular advantage of the method according to the invention that siloxanes are formed as coupling products during the thermolysis of the third organosilicon compound, for example a compound of general formula IV, in addition to the target compound, i.e., an isocyanate compound. The siloxanes in the simplest case are disiloxanes. Scheme 10 shows the thermolysis of a compound of general formula IV, wherein a disiloxane of general formula VIII is formed in addition to the compound of general formula I:

(Scheme 10)

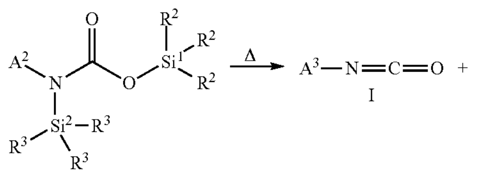

-continued

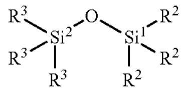

VIII

In the compound of general formula VIII $R^2$ at each occurrence have the meanings given in connection with the compound of general formula II and $R^3$ at each occurrence have the meanings given in connection with the compound of general formula III. If all of $R^2$ and all of $R^3$ each are methyl, then the compound of general formula VIII is hexamethyl disiloxane. Hexamethyl disiloxane is used in various ways, e.g., it can be converted to trimethylsilyl halide with halogens or hydrohalic acid. Moreover, it is used in the preparation of silicone oils for adjusting the molar mass distributions.

The term "aliphatic", unless stated otherwise, relates to a branched or unbranched or cyclic hydrocarbon component including a component containing both cyclic and chain elements which may be completely saturated or mono- or polyunsaturated. Examples of saturated hydrocarbon components comprise alkyl groups, alkylene groups and cycloalkyl groups. Examples of unsaturated hydrocarbon components comprise alkenyl groups and alkynyl groups. The aliphatic hydrocarbon component may optionally contain one or more, for example one to four hetero atoms selected from the group consisting of O, N, S, Si, and Ge.

The term "aromatic", unless stated otherwise, relates to a hydrocarbon component having at least one aromatic ring, including a component containing both at least one aromatic and at least one chain element which may be completely saturated or mono or polyunsaturated. Examples of aromatic rings comprise aryl groups, heteroaryl groups, arylene groups and heteroarylene groups. Examples of chain elements comprise alkylene groups. Examples of aromatic groups containing at least one aromatic ring and at least one chain element comprise alkylene arylene groups, arylene bis(alkylene) groups and alkylene bis(arylene) groups. The aromatic hydrocarbon component may optionally contain one or more, for example one to four hetero atoms selected from the group consisting of O, N, S, Si, and Ge.

The term "alkyl", unless stated otherwise, in particular relates to a saturated aliphatic hydrocarbon group with a branched or unbranched carbon chain with 1 to 12 carbon atoms, preferably 1 to 8 carbon atoms, and particularly preferred 1 to 6 carbon atoms. Examples of alkyl groups comprise, but are not limited to methyl, ethyl, propyl, isopropyl, isobutyl, sec-butyl, tert-butyl, pentyl, n-hexyl, octyl, dodecyl, and the like. The alkyl group may optionally be substituted with one or more substituents, wherein each substituent independently is alkyl, alkoxy, halogen, haloalkyl, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or a siloxane group, unless specifically stated otherwise. The alkyl group may be partially fluorinated or perfluorinated. The alkyl group may optionally contain one or more heteroatoms selected from the group consisting of O, N, S, Si, and Ge. The alkyl group can contain one or more chains consisting of two or more, for example 2 to 12 Si atoms.

The term "heteroalkyl", unless stated otherwise, relates to an alkyl group, as defined herein, wherein one, two or three hydrogen atoms have been replaced by substituents independently selected from the group consisting of $—OR^a$, $—NR^bR^c$, $—S(O)_wR^d$ (wherein w is an integer from 0 to 2), $SiR^z_3$, $Si(OR^z)_3$ and $SiR^z(OR^z)_2$, with the proviso that the site of attachment of the heteroalkyl residue is a carbon atom, wherein $R^a$ is acyl, alkyl, cycloalkyl, or cycloalkylalkyl; $R^b$ and $R^c$ independently are acyl, alkyl, cycloalkyl or cycloalkylalkyl; and if w is 0, $R^d$ is alkyl, cycloalkyl, or cycloalkylalkyl, and if w is 1 or 2, $R^d$ is alkyl, cycloalkyl, or cycloalkylalkyl; $R^z$ at each occurrence independently is hydrogen or alkyl, as defined herein, except for $SiH_3$.

The term "cycloalkyl", unless stated otherwise, in particular relates to saturated, carbocyclic groups consisting of mono or bicyclic rings and having 3 to 12 ring atoms. The cycloalkyl group can optionally be substituted with one or more substituents, wherein each substituent independently is alkyl, alkoxy, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or a siloxane group, unless specifically stated otherwise. Examples of cycloalkyl groups comprise, but are not limited to cyclopropyl, cyclobutyl, cyclopentyl, cyclohexyl, cycloheptyl, and the like. The cycloalkyl group may be partially fluorinated or perfluorinated. The cycloalkyl group can optionally contain one or more hetero atoms selected from the group consisting of O, N, S, Si, and Ge.

The term "heterocycloalkyl", unless stated otherwise, relates to a saturated cyclic ring with 5 to 12 ring atoms, wherein 1 to 4 of the ring atoms are heteroatoms selected from one or more of N, O, and S and the remaining ring atoms are carbon atoms. Examples of heterocycloalkyl groups comprise, but are not limited to piperidinyl, piperazinyl, homopiperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, quinuclidinyl, tetrahydrofuryl, tetrahydropyranyl, thiomorpholinyl, dihydroquinolinyl, and 1,4-diazepane. The heterocycloalkyl group can optionally be substituted with one or more substituents, wherein each substituent independently is alkyl, alkoxy, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or is a siloxane group, unless specifically stated otherwise. The heterocycloalkyl group can be partially fluorinated or perfluorinated.

The term "alkenyl", unless stated otherwise, in particular relates to an unsaturated aliphatic hydrocarbon group with a branched or unbranched carbon chain with 2 to 12 carbon atoms, preferably 2 to 8 carbon atoms and especially preferred 2 to 6 carbon atoms which has at least one olefinic double bond and more preferably a single double bond. Examples of alkenyl groups comprise, but are not limited to vinyl, allyl, methallyl, 1,1-dimethylallyl, propenyl, butenyl, pentadienyl, hexenyl, octenyl, and the like. An allyl group is preferred. The alkenyl group can optionally be substituted with one or more substituents, wherein each substituent independently is alkyl, alkoxy, halogen, haloalkyl, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or is a siloxane group, unless specifically stated otherwise. The alkenyl group can be partially fluorinated or perfluorinated. The alkenyl group can optionally contain one or more heteroatoms selected from the group consisting of O, N, S, Si, and Ge. The alkenyl group can contain one or more chains consisting of two or more, for example 2 to 12 Si atoms.

The term "alkynyl", unless stated otherwise, in particular relates to an unsaturated aliphatic hydrocarbon group with a branched or unbranched carbon chain with 2 to 12 carbon atoms, preferably 2 to 8 carbon atoms and especially preferred 2 to 6 carbon atoms which has at least one olefinic triple bond and more preferably a single triple bond. Examples of alkynyl groups comprise, but are not limited to acetylenyl, propargyl, n-but-2-yn-1-yl and the like. A propargyl group is preferred. The alkynyl group can optionally be substituted with one or more substituents, wherein each substituent independently is alkyl, alkoxy, halogen, haloalkyl, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or is a siloxane group, unless specifically stated otherwise. The alkynyl group can optionally contain one or more heteroatoms selected from the group consisting of O, N, S, Si, and Ge. The alkynyl group can contain one or more chains consisting of two or more, for example 2 to 12 Si atoms.

The term "alkoxy", unless stated otherwise, in particular relates to a group of formula —OR, wherein R is an alkyl group, as defined herein. Examples of alkoxy components comprise, but are not limited to methoxy, ethoxy, isopropoxy, and the like. The alkoxy group can optionally be substituted with one or more substituents, wherein each substituent independently is alkyl, alkoxy, halogen, haloalkyl, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or is a siloxane group, unless specifically stated otherwise.

The term "acyl" relates to a group of formula —C(=O)R, wherein R is alkyl, as defined herein.

The term "halogen" relates to fluorine, chlorine, bromine, or iodine.

The term "aryl", unless stated otherwise, relates to a cyclic, aromatic hydrocarbon group consisting of a mono or bicyclic aromatic ring system with 5 to 10 ring atoms, preferably 5 or 6 ring atoms, or having such a ring system. The aryl group can optionally be a substituted aryl group. Examples of aryl groups comprise, but are not limited to phenyl, naphthyl, naphthalenyl, fluorenyl, indenyl, pentalenyl, azulenyl, oxydiphenyl, biphenyl, methylendiphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylendioxyphenyl, ethylendioxyphenyl, and the like, including partially hydrogenated derivatives thereof. The term "substituted aryl group" in particular relates to an aryl group which optionally is independently substituted with one to four substituents, preferably one or two substituents selected from alkyl, cycloalkyl, heteroalkyl, halogen, alkoxy, amino, acylamino, monoalkylamino, dialkylamino, $SiR^z_3$, $Si(OR^z)_3$, $SiR^z(OR^z)_2$ (wherein $R^z$ at each occurrence independently is hydrogen or alkyl, as defined herein, except for $SiH_3$), a siloxane group, haloalkyl, haloalkoxy, alkane sulphonyl, —COR (wherein R is alkyl, phenyl or phenylalkyl), $-(CR'R'')_n-COOR$ (wherein n is an integer from 0 to 5, R' and R" independently are hydrogen or alkyl, and R is alkyl, cycloalkyl, cycloalkylalkyl, phenyl, or phenylalkyl) or $-(CR'R'')_n-CONR^{a'}R^{b'}$ (wherein n is an integer from 0 to 5, R' and R" independently are hydrogen or alkyl, and $R^{a'}$ and $R^{b'}$ independently are alkyl, cycloalkyl, cycloalkylalkyl, phenyl, or phenylalkyl).

The term "heteroaryl", unless stated otherwise, relates to a monocyclic or bicyclic group with 5 to 10, more preferably 5 to 6 ring atoms with at least one aromatic ring and further containing one, two, three, or four ring hetero atoms selected from N, O and S, wherein the remaining ring atoms are C. The heteroaryl can optionally be substituted with one, two, three, or four substituents, wherein each substituent independently is amino, or for the non-aromatic part of the cyclic ring also by oxo, unless specifically stated otherwise. Examples of heteroaryl groups comprise, but are not limited to optionally substituted imidazolyl, optionally substituted oxazolyl, optionally substituted thiazolyl, optionally substituted pyrazinyl, optionally substituted pyrrolyl, optionally substituted pyridinyl, optionally substituted pyrimidinyl, optionally substituted indonyl, optionally substituted isoquinolinyl, optionally substituted carbazol-9-yl, optionally substituted furanyl, optionally substituted benzofuranyl, optionally substituted benzo[1,2,3]thiadiazolyl, optionally substituted benzo[b]thiophenyl, optionally substituted 9h-thioxanthenyl, and optionally substituted thieno[2,3-c] pyridinyl.

The term "alkylaryl", unless stated otherwise, in particular relates to a group of formula —$R^gR^h$, wherein $R^g$ is an arylene group and $R^h$ is an alkyl group, as defined herein. The alkylaryl group can optionally be a substituted alkylaryl group. Examples of alkylaryl groups comprise, but are not limited to o-tolyl, m-tolyl, p-tolyl, o-tert-butylphenyl, m-tert-butylphenyl, p-tert-butylphenyl, and the like.

The term "arylalkyl", unless stated otherwise, in particular relates to a group of formula —$R^eR^f$, wherein $R^e$ is an alkylene group and $R^f$ is an aryl group, as defined herein. The arylalkyl group can optionally be a substituted arylalkyl group. Examples of arylalkyl groups comprise, but are not limited to benzyl, phenylethyl, 3-(3-chlorophenyl)-2-methylpentyl, and the like.

Here, the term "alkylene" in particular relates to a divalent saturated aliphatic hydrocarbon group with a branched or unbranched carbon chain with 1 to 12 carbon atoms, preferably 1 to 8 carbon atoms and especially preferred 1 to 6 carbon atoms. Examples of alkylene groups comprise, but are not limited to methylene, ethylene, propylene, butylene, and the like. The alkylene group can optionally be substituted with one or more substituents, wherein each substituent independently is alkyl, alkoxy, halogen, haloalkyl, amino, monoalkylamino, dialkylamino, $SiR^z_3$, $Si(OR^z)_3$, $SiR^z(OR^z)_2$, wherein $R^z$ at each occurrence independently is hydrogen or alkyl, as defined herein, except for $SiH_3$, or is a siloxane group, unless specifically stated otherwise. The alkylene group can be partially fluorinated or perfluorinated. The alkylene group can optionally contain one or more hetero atoms selected from the group consisting of O, N, S, Si, and Ge. The alkylene group can contain one or more chains consisting of two or more, for example 2 to 12 Si atoms.

The term "arylene", unless stated otherwise, relates to a divalent cyclic, aromatic hydrocarbon group consisting of a mono or bicyclic aromatic ring system with 5 to 10 ring atoms, preferably 5 or 6 ring atoms. The arylene group can optionally be a substituted arylene group. Examples of arylene groups comprise, but are not limited to phenylene, naphthylene. The term "substituted arylene group" in particular relates to an arylene group which is optionally independently substituted with one to four substituents, preferably one or two substituents selected from alkyl, cycloalkyl, heteroalkyl, halogen, alkoxy, amino, acylamino, monoalkylamino, dialkylamino, $SiR^z_3$, $Si(OR^z)_3$, $SiR^z(OR^z)_2$ (wherein $R^z$ at each occurrence independently is hydrogen or alkyl, as defined herein, except for $SiH_3$), a siloxane group, haloalkyl, haloalkoxy, alkane sulphonyl, —COR (wherein R is alkyl, phenyl, or phenylalkyl), —$(CR'R'')_n$—COOR (wherein n is an integer from 0 to 5, R' and R'' independently are hydrogen or alkyl, and R is alkyl, cycloalkyl, cycloalkylalkyl, phenyl, or phenylalkyl) or —$(CR'R'')_n$—$CONR^{a'}R^{b'}$ (wherein n is an integer from 0 to 5, R' and R'' independently are hydrogen or alkyl and $R^{a'}$ and $R^{b'}$ independently are alkyl, cycloalkyl, cycloalkylalkyl, phenyl, or phenylalkyl).

The term "heteroarylene", unless stated otherwise, relates to a divalent cyclic, aromatic hydrocarbon group consisting of a mono or bicyclic aromatic ring system with 5 to 10 ring atoms, preferably 5 or 6 ring atoms, wherein the ring system contains one, two, three, or four ring hetero atoms selected from N, O, and S, wherein the remaining ring atoms are C. The heteroarylene group can optionally be a substituted heteroarylene group. Examples of heteroarylene groups comprise, but are not limited to pyrenylene and furylene. The term "substituted heteroarylene group" in particular relates to a heteroarylene group which is optionally independently substituted with one to four substituents, preferably one or two substituents selected from alkyl, cycloalkyl, heteroalkyl, halogen, alkoxy, amino, acylamino, monoalkylamino, dialkylamino, $SiR^z_3$, $Si(OR^z)_3$, $SiR^z(OR^z)_2$ (wherein $R^z$ at each occurrence independently is hydrogen or alkyl, as defined herein, except for $SiH_3$), a siloxane group, haloalkyl, haloalkoxy, alkane sulphonyl, —COR (wherein R is alkyl, phenyl, or phenylalkyl), —$(CR'R'')_n$—COOR (wherein n is an integer from 0 to 5, R' and R'' independently are hydrogen or alkyl, and R is alkyl, cycloalkyl, cycloalkylalkyl, phenyl, or phenylalkyl) or —$(CR'R'')_n$—$CONR^{a'}R^{b'}$ (wherein n is an integer from 0 to 5, R' and R'' independently are hydrogen or alkyl and $R^{a'}$ and $R^{b'}$ independently are alkyl, cycloalkyl, cycloalkylalkyl, phenyl, or phenylalkyl).

The term "alkylene-arylene", unless stated otherwise, in particular relates to a group of formula —$R'''R''$—, wherein $R'''$ is an arylene group and $R''$ is an alkylene group, as defined herein. The alkylene-arylene group can optionally be a substituted alkylene-arylene group. Examples of alkylene arylene groups comprise, but are not limited to phenylene-methylene, phenylene-ethylene, phenylene-n-propylene, and the like.

The term "arylene-bis(alkylene)", unless stated otherwise, in particular relates to a group of formula —$R''R'''R''$—, wherein $R'''$ is an arylene group and $R''$ at each occurrence independently each is an alkylene group, as defined herein. The arylene-bis(alkylene) can optionally be a substituted arylene bis(alkylene). Examples of arylene-bis(alkylene) comprise, but are not limited to phenylene-bis(methylene), phenylene-bis(ethylene), phenylene-bis(n-propylene), and the like.

The term "alkylene-bis(arylene)", unless stated otherwise, in particular relates to a group of formula —$R'''R''R'''$—, wherein $R'''$ at each occurrence each independently is an arylene group and $R''$ is an alkylene group, as defined herein. The alkylene-bis(arylene) can optionally be a substituted alkylene-bis(arylene). Examples of alkylene-bis(arylene) comprise, but are not limited to methylene-bis(phenylene), ethylene-bis(phenylene), n-propylene-bis(phenylene), and the like.

According to the invention further provided is the use of a compound of general formula II (formula II)

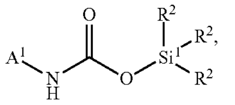

wherein $A^1$ is $R^1$ or a group of general formula G-III:

(formula G-III)

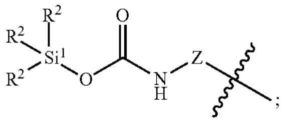

$R^1$ is a substituted or unsubstituted, aliphatic or aromatic group; and $R^2$ at each occurrence each independently is selected from the group consisting of hydrogen, a substituted or unsubstituted alkyl group with 1 to 12 carbon atoms and a substituted or unsubstituted aryl group, with the proviso that at least one residue $R^2$ which is not hydrogen is bound to each silicon atom $Si^1$;

Z is a substituted or unsubstituted, aliphatic or aromatic group;

for the preparation of an isocyanate compound of general formula I $A^3$-N=C=O (formula I), wherein $A^3$ is $R^1$ or a group of formula G-V:

O=C=N—Z- (formula G-V)

$R^1$ and Z have the meanings given in connection with the compound of general formula II.

According to the invention additionally provided is the use of a compound of general formula IV (formula IV)

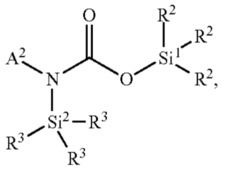

wherein $A^2$ is $R^1$ or a group of general formula G-IV:

(formula G-IV)

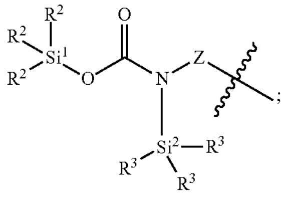

$R^1$ is a substituted or unsubstituted, aliphatic or aromatic group; and $R^2$ at each occurrence each independently is selected from the group consisting of hydrogen, a substituted or unsubstituted alkyl group with 1 to 12 carbon atoms and a substituted or unsubstituted aryl group, with the proviso that at least one residue $R^2$ which is not hydrogen is bound to each silicon atom $Si^1$;

$R^3$ at each occurrence has the meanings given in connection with the compound of general formula III;

Z is a substituted or unsubstituted, aliphatic or aromatic group;

for the preparation of an isocyanate compound of general formula I $A^3$-N=C=O (formula I), wherein $A^3$ is $R^1$ or a group of formula G-V:

O=C=N—Z- (formula G-V)

$R^1$ and Z have the meanings given in connection with the compound of general formula II.

Details on the uses according to the invention are found in the description of the method according to the invention.

The method according to the invention and the uses according to the invention provide a safe, phosgene-free synthesis pathway for isocyanates. Here, cost-effective raw materials are used, isocyanates are obtained in high yields and high purity and coupling products are obtained that can be used as by-products, i.e., siloxanes. The synthesis pathway has a low energy consumption. This, among others, is due to the fact that the synthesis pathway is associated with less reaction heats. Moreover, the synthesis pathway requires no catalysts. The method according to the invention in particular enables safe and economic synthesis of diisocyantes. Said diisocyantes may be used as monomers for the preparation of polyurethanes. The method according to the invention and the uses according to the invention are particularly suitable for the preparation of aromatic isocyanates, in particular of isocyanates in which $R^1$ is aryl, such as phenyl, or Z contains an arylene group, such as phenylene or phenylene-bis(methylene).

In the following, the invention is explained in detail with reference to examples not intended to limit the invention.

In the examples preparation of the isocyanates 11, 12, and 16 starting with primary amines is described. Isocyanates 11 and 12 may be prepared in accordance with the four-stage synthesis pathway shown in scheme 11.

Scheme 11

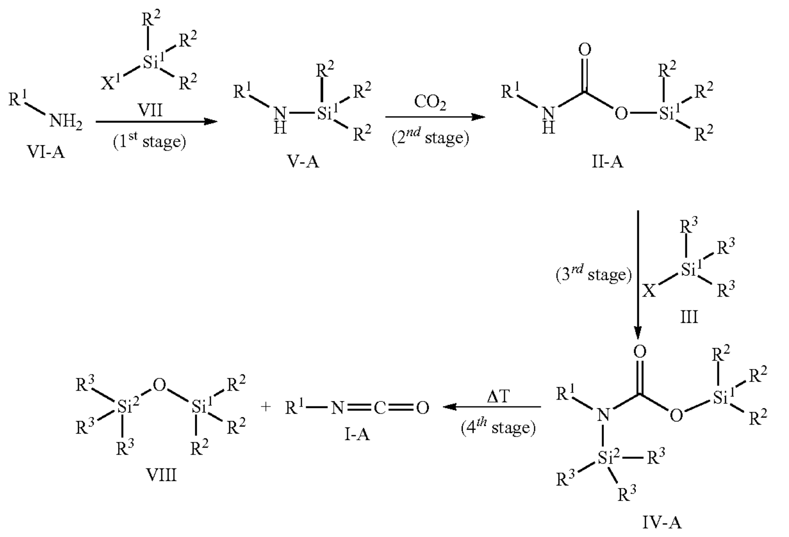

VI-A, V-A, II-A, III, IV-A, I-A, VIII

Scheme 11 shows a variant of the four-stage synthesis pathway shown in scheme 9 which is suitable for the preparation of monoisocyanates. With respect to scheme 11, in example 1 $R^1$ is phenyl, $R^2$ and $R^3$ at each occurrence are methyl, $X^1$ is chlorine, and X is triflate. In example 2 $R^1$ is n-octyl, $R^2$ and $R^3$ at each occurrence are methyl, $X^1$ is chlorine and X is triflate.

With the procedure shown in scheme 11 it is also possible to prepare benzylisocyanate, for example. With respect to scheme 11, in this case $R^1$ is benzyl, $R^2$ and $R^3$ at each occurrence are methyl, $X^1$ is chlorine and X is triflate.

Isocyanate 16 may be prepared in accordance with the four-stage synthesis pathway shown in scheme 12.

Scheme 12

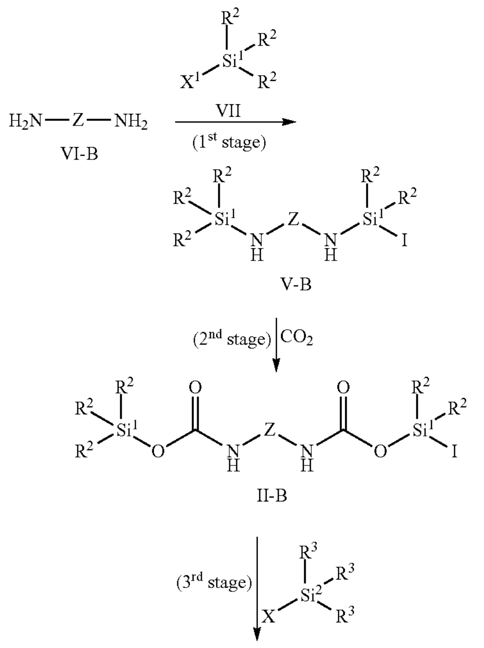

VI-B, V-B, II-B

-continued

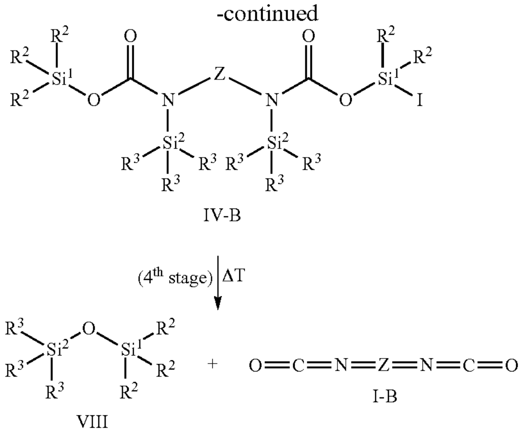

IV-B, VIII, I-B

Scheme 12 shows a variant of the four-stage synthesis pathway shown in scheme 9 which is suitable for the preparation of diisocyanates. With respect to scheme 12, in example 3 Z is $-(CH_2)_8-$, $R^2$ and $R^3$ at each occurrence are methyl, $X^1$ is chlorine and X is triflate.

With the procedure shown in scheme 12 it is also possible to prepare 1,3-bis(isocyanatomethyl)benzene which is also referred to as m-xylylene-di-isocynate. With respect to scheme 12, in this case Z is 1,3-phenylene-bis(methylene), $R^2$ and $R^3$ at each occurrence are methyl, $X^1$ is chlorine and X is triflate.

Example 1

Synthesis of phenylisocyanate (11)

Phenylisocyanate (compound 11) was prepared according to the methods shown in scheme 11. Phenylisocyanate is an example of an aromatic monoisocyanate.

Stage 1: Synthesis of Aminosilane

First, 4.28 g (46.00 mmol) of aniline were provided together with 5.10 g (50.50 mmol) of triethylamine in 100 ml of n-pentane. 5.12 g (47.16 mmol) of trimethylchlorosilane are added under stirring in an ice bath via a dropping funnel. Upon adding the silane dropwise formation of a white solid as well as the development of white smoke could be observed. After the chlorosilane was completely added, the mixture was heated to room temperature and stirred for 24 hours. After the white solid has been removed by filtration and the solvent has been removed under reduced pressure, 7.13 g (43.14 mmol) of N-trimethylsilylaniline could be obtained as a clear, colorless liquid. The yield is 94%. The purity of the product was confirmed by NMR spectroscopy.

$^{1}$H-NMR (400 MHz, $C_6D_6$, δ [ppm]): 7.08-6.43 (m, 5H, ArH), 3.46 (s, 1H, NH), 0.15 (s, 9H, SiMe3). $^{13}$C-NMR (101 MHz, $C_6D_6$, δ [ppm]): 148.1 (ArC), 129.6 (ArCH), 117.9 (ArCH), 116.7 (ArCH), 0.2 (SiMe3). $^{29}$Si-NMR (79 MHz, $C_6D_6$, δ [ppm]): 2.1.

Stage 2: $CO_2$ Insertion 7.56 g (45.7 mmol) of N-trimethylsilylaniline were mixed with 20 ml of dry tetrahydrofuran (THF) and filled into a large autoclave under inert conditions. The autoclave was pressurized with a $CO_2$ excess pressure of 8 bar and allowed to stand under these conditions for 24 hours. The pressure was periodically controlled. After the reaction time has expired the clear, pale yellow reaction mixture was inert transferred to a Schlenk vessel. After a few minutes formation of colorless crystal needles could be observed. The solvent was removed under reduced pressure and the white solid obtained was dried in vacuum for 3 hours. In this way, 8.62 g (41.17 mmol) of N-phenyl-O-trimethylsilyl-carbamate could be obtained in a yield of 90%. The identity and purity of the target compound were confirmed by NMR spectroscopy.

$^{1}$H-NMR (400 MHz, THF-d8, δ [ppm]): 8.64 (s, 1H, NH), 7.46-6.92 (m, 5H, ArH), 0.30 (s, 9H, SiMe3). $^{13}$C-NMR (101 MHz, THF-d8, δ [ppm]): 153.0 (CO), 140.8 (ArC), 129.4 (ArCH), 123.1 (ArCH), 118.9 (ArCH), 0.1 (SiMe3). $^{29}$Si-NMR (79 MHz, THF-d8, δ [ppm]): 22.2. Elemental analysis: calculated N, 6.69%, C, 57.38%, H, 7.22%; measured N, 6.79%, C, 57.14%, H, 7.053%.

Stage 3: Silylation 6.87 g (32.82 mmol) of N-phenyl-O-trimethylsilyl-carbamate were dissolved in 100 ml of n-pentane together with 3.40 g (33.60 mmol) of triethylamine. The mixture was stirred in the ice bath. 7.28 g (32.76 mmol) of trimethylsilyltriflate were added dropwise via a dropping funnel. Formation of a flake-like second phase could be observed. Subsequently, the mixture was heated to room temperature and stirred at this temperature for 2 hours. The second phase formed was congealed in a cold mixture of dry ice and isopropanol and the supernatant solution was decanted off. The solvent was removed under reduced pressure, whereby precipitation of a white solid could be observed. The solid was dried in vacuum for 2 hours. In this way, 7.69 g (27.32 mmol) of N,O-bis(trimethylsilyl)-N-phenyl-carbamate (1) could be obtained in a yield of 83%. The identity and purity of the target product were confirmed by NMR spectroscopy and single-crystal X-ray analysis.

$^{1}$H-NMR (400 MHz, $CDCl_3$, δ [ppm]): 7.11-6.84 (m, 5H, ArH), 0.12 (s, 9H, SiMe3). $^{13}$C-NMR (101 MHz, $CDCl_3$, δ [ppm]): 157.1 (CO), 141.6 (ArC), 128.7 (ArCH), 126.5 (ArCH), 119.5-116.1 (ArCH), 0.7 (SiMe3). $^{29}$Si-NMR (79 MHz, $CDCl_3$, δ [ppm]): 23.4, 10.7. Elemental analysis: calculated N, 4.98%, C, 55.47%, H, 8.24%; measured N, 5.07%, C, 55.01%, H, 8.215%.

Stage 4: Thermolysis

A few grams of N,O-bis(trimethylsilyl)-N-phenyl-carbamate (1) were filled into the still pot of the kugelrohr distillation apparatus under inert conditions. The still pot and the middle pot were put into the heating chamber (tubular furnace), while the outer pot was cooled in the water bath. A temperature profile was run at a rotation of 20 rotations per minutes (rpm). The furnace was heated to 170° C. for 30 minutes, subsequently the temperature was increased to 200° C. for another 30 minutes, and finally heated to 230° C. also for 30 min. After the solid used was melted accumulation of colorless liquid both in the middle and in the outer pot could be observed. After the reaction time has expired, the pots were cooled to room temperature and inert transferred to Schlenk vessels. The composition was analyzed by NMR spectroscopy. While in the middle pot there was still found undecomposed carbamate, in the $^{29}$Si-NMR spectrum of the outer pot only the presence of hexamethyldisiloxane was shown. These results are confirmed by the $^{13}$C-NMR spectra. In addition, in the $^{13}$C-NMR spectra of the middle and outer pots a signal at 134.0 ppm each was shown which can clearly assigned to the phenyl isocyanate. While in the middle pot a variety of other signals is indicative of a mixture of substances of various species, only the isocyanate together with hexamethyldisiloxane is found in the sample of the outer pot ($^{13}$C: δ=2.0 ppm). Further, presence of the isocyanate was rechecked by IR-ATR spectroscopy. Again, the isocyanate band at 2258 $cm^{-1}$ was clearly identified. Comparing both analyses with a commercially available sample of the phenylisocyanate provided exact matches.

Example 2

Synthesis of n-octyl-isocyanate (12)

n-Octyl-isocyanate (compound 12) was prepared according to the method shown in scheme 11. n-Octyl-isocyanate is an example of an aliphatic monoisocyanate.

Stage 1: Synthesis of Aminosilane

First, 6.02 g (46.56 mmol) of n-octylamine were provided together with 4.79 g (47.31 mmol) of triethylamine in 100 ml of diethyl ether. 5.04 g (46.39 mmol) of trimethyl chlorosilane were added under stirring in the ice bath via a dropping funnel. When adding the silane dropwise formation of a white solid and development of white smoke was observed. Subsequently, the mixture was heated to room temperature and stirred for 24 hours. After having removed the white solid by filtration and the solvents under reduced pressure, 8.11 g (40.24 mmol) of N-trimethylsilyl-n-octylamine were obtained as a clear, colorless liquid in a yield of 87%. Purity of the product was confirmed by NMR spectroscopy.

$^{1}$H-NMR (400 MHz, $CDCl_3$, δ [ppm]): 2.81 (t, 2H, $CH_2$), 1.50-1.40 (m, 12H, $CH_2$), 1.01 (t, 3H, $CH_3$), 0.49 (s, 1H, NH), 0.15 (s, 9H, SiMe3). $^{13}$C-NMR (101 MHz, $CDCl_3$, δ [ppm]): 42.0 ($CH_2$), 35.0 ($CH_2$), 32.1 ($CH_2$), 29.7 ($CH_2$), 29.5 ($CH_2$), 27.1 ($CH_2$), 22.8 ($CH_2$), 14.1 ($CH_3$), 0.0 (SiMe3). $^{29}$Si-NMR (79 MHz, $CDCl_3$, δ [ppm]): 3.0.

Stage 2: $CO_2$ Insertion 8.1 g (40.24 mmol) of N-trimethylsilyl-n-octylamine were mixed with 44 ml of dry THF and cooled in the ice bath. Gas entry of $CO_2$ took place for 30 minutes while constantly stirring the reaction mixture. Subsequently, the solvent was removed by cold distillation and the insertion product was recovered as a clear, colorless liquid. 8.68 g (35.35 mmol) of N,n-octyl-O-trimethylsilyl-carbamate were obtained which corresponds to a yield of 88%. The identity and purity of the target compound were confirmed by NMR spectroscopy.

$^{1}$H-NMR (400 MHz, $CDCl_3$, δ [ppm]): 5.54 (s, 1H, NH), 3.10 (t, 2H, $CH_2$), 1.49-1.29 (m, 12H, $CH_2$), 0.88 (t, 3H, $CH_3$), 0.26 (s, 9H, SiMe3). $^{13}$C-NMR (101 MHz, $CDCl_3$, δ [ppm]): 155.5 (CO), 41.1 ($CH_2$), 31.9 ($CH_2$), 30.1 ($CH_2$), 29.4 ($CH_2$), 27.0 ($CH_2$), 25.7 ($CH_2$), 22.7 ($CH_2$), 14.1 ($CH_3$), 0.0 (SiMe3). $^{29}$Si-NMR (79 MHz, $CDCl_3$, δ [ppm]): 21.7.

Stage 3: Silylation 8.68 g (35.35 mmol) of N,n-octyl-O-trimethylsilyl-carbamate were dissolved in 100 ml of n-pentane together with 3.64 g (35.99 mmol) of triethylamine and stirred in the ice bath. 8.05 g (36.23 mmol) of trimethylsilyltriflate were added dropwise via a dropping funnel. Formation of a second phase at the bottom of the Schlenk flask was observed. Subsequently, the mixture was stirred at room temperature for 3 hours. The 2$^{nd}$ phase formed was congealed in the dry ice/isopropanol cold mixture and the supernatant solution was decanted off. The solvent was removed by cold distillation thereby leaving a pale yellow, clear liquid in the reaction flask. In this way, 8.83 g (27.81 mmol) of N,O-bis(trimethylsilyl)-N,n-octyl-carbamate (2) were obtained. This corresponds to a yield of 79%. The identity and purity of the target compound were confirmed by NMR spectroscopy.

$^{1}$H-NMR (400 MHz, $CDCl_3$, δ [ppm]): 5.37 (s, 1H, NH), 3.01 (t, 2H, $CH_2$), 1.38-1.20 (m, 12H, $CH_2$), 0.80 (t, 3H, $CH_3$), 0.20 (s, 9H, SiMe3), 0.14 (s, 9H, SiMe3). $^{13}$C-NMR (101 MHz, $CDCl_3$, δ [ppm]): 157.6 (CO), 44.8 ($CH_2$), 32.0 ($CH_2$), 31.1 ($CH_2$), 29.7 ($CH_2$), 29.5 ($CH_2$), 27.2 ($CH_2$), 22.8 ($CH_2$), 14.2 ($CH_3$), 0.8 (SiMe3), 0.0 (SiMe3). $^{29}$Si-NMR (79 MHz, $CDCl_3$, δ [ppm]): 21.3, 8.8.

Stage 4: Thermolysis

A few milliliters of N,O-bis(trimethylsilyl)-N,n-octyl-carbamate (2) were filled into the still pot of the kugelrohr distillation apparatus under inert conditions. The still pot and the middle pot were put into the heating chamber (tubular furnace), while the outer pot was cooled in the water bath. The carbamate was heated to 300° C. for 2 hours, while the kugelrohr distillation apparatus was continuously rotated with 20 rpm. A colorless liquid accumulated in the outer pot. The middle pot at the end of the reaction time contained a yellow liquid, and the still pot was almost empty. Subsequently, the pots were cooled to room temperature and inert transferred to Schlenk vessels. The composition was analyzed by NMR spectroscopy. While in the middle pot there was still found undecomposed carbamate, in the $^{29}$Si-NMR spectrum of the outer pot only the presence of hexamethyldisiloxane was shown. These results are confirmed by the $^{13}$C-NMR spectra. In addition, in the $^{13}$C-NMR spectra of the outer pot a signal at 120.5 ppm each was shown which can clearly assigned to the n-octyl isocyanate. While in the middle pot a variety of other signals is indicative of a mixture of substances of various species, only the isocyanate together with hexamethyldisiloxane is found in the sample of the outer pot ($^{13}$δ: 6=2.0 ppm). Comparing the analysis with a commercially available sample of the n-octyl isocyanate provided exact matches.

Example 3

Synthesis of 1,8-diisocyanatooctane (16)

1,8-Diisocyanatooctane (compound 16) was prepared according to the method shown in scheme 12. 1,8-Diisocyanatooctane is an example of an aliphatic diisocyanate.

Stage 1: Synthesis of Aminosilane

First, 3.10 g (21.52 mmol) of 1,8-diaminooctane together with 5.12 g (50.63 mmol) of triethylamine were provided in 140 ml diethyl ether. 4.99 g (45.97 mmol) of trimethyl chlorosilane were added under stirring in the ice bath via a dropping funnel. When adding the silane dropwise formation of a white solid and development of white smoke was observed. After having completely added the chlorosilane the mixture was stirred over night at room temperature. After having removed the white solid by filtration and the solvents under reduced pressure the aminosilane was obtained as a colorless liquid. In this way, 4.71 g (16.33 mmol) of N,N'-bis(trimethylsilyl)-1,8-diaminooctane were obtained. The yield is 76%. Purity of the product was confirmed by NMR spectroscopy.

$^{1}$H-NMR (400 MHz, $CDCl_3$, δ [ppm]): 2.81 (m, 4H, $CH_2$), 1.49-1.41 (m, 12H, $CH_2$), 0.45 (s, 2H, NH), 0.15 (s, 18H, SiMe3). $^{13}$C-NMR (101 MHz, $CDCl_3$, δ [ppm]): 41.9 ($CH_2$), 34.9 ($CH_2$), 29.6 ($CH_2$), 26.9 ($CH_2$), 0.0 (SiMe3). $^{29}$Si-NMR (79 MHz, $CDCl_3$, δ [ppm]): 2.9.

Stage 2: $CO_2$ Insertion 7.04 g (24.39 mmol) of N,N'-bis(trimethylsilyl)-1,8-diaminooctane were mixed with 40 ml of dry THF. $CO_2$ insertion was by gas entry for 20 minutes, while the reaction mixture was stirred and cooled in the ice bath. The solvent was removed under reduced pressure and the white solid obtained was dried in vacuum. In this way, 8.52 g (22.62 mmol) of 1,8-[O,O'-bis(trimethylsilyl)-carbamato]-octane were obtained in a yield of 93%. The identity and purity of the target compound were confirmed by NMR spectroscopy.

$^{1}$H-NMR (400 MHz, $CDCl_3$, δ [ppm]): 6.05 (s, 2H, NH), 3.06 (m, 4H, $CH_2$), 1.46-1.31 (m, 12H, $CH_2$), 0.08 (s, 18H, SiMe3). $^{13}$C-NMR (101 MHz, $CDCl_3$, δ [ppm]): 155.6 (CO), 41.2 ($CH_2$), 30.2 ($CH_2$), 29.6 ($CH_2$), 27.1 ($CH_2$), 0.0 ($SiMe_3$). $^{29}$Si-NMR (79 MHz, $CDCl_3$, δ [ppm]): 20.9.

Stage 3: Silylation 6.22 g (16.53 mmol) of 1,8-[O,O'-bis(trimethylsilyl)-carbamato]-octane were dissolved in 50 ml of anisole with 3.37 g (33.34 mmol) of triethylamine. The mixture was stirred in the ice bath. 7.38 g (33.19 mmol) of trimethylsilyltriflate were added dropwise via a dropping funnel. Formation of a flake-like second phase was observed. Subsequently, the mixture was heated to room temperature and stirred at this temperature for 2 hours. The second phase formed was congealed in a cold mixture of dry ice and isopropanol and the supernatant solution was decanted off. The solvent was removed under reduced pressure thereby precipitation of a white solid was observed. The solid was dried in vacuum for 4 hours. In this way, 8.12 g (15.58 mmol) of 1,8-[N,N',O,O'-tetrakis(trimethylsilyl)-carbamato]-octane (6) were obtained which corresponds to a yield of 94%. The identity and purity of the target compound were confirmed by NMR spectroscopy.

$^{1}$H-NMR (400 MHz, $CDCl_3$, δ [ppm]): 8.78 (s, 2H, NH), 3.07 (m, 4H, $CH_2$), 1.44-1.26 (m, 12H, $CH_2$), 0.29 (s, 18H, SiMe3), 0.22 (s, 18H, SiMe3). $^{13}$C-NMR (101 MHz, $CDCl_3$, δ [ppm]): 157.1 (CO), 44.8 ($CH_2$), 30.9 ($CH_2$), 29.5 ($CH_2$), 27.0 ($CH_2$), 0.8 (SiMe3), 0.0 (SiMe3). $^{29}$Si-NMR (79 MHz, $CDCl_3$, δ [ppm]): 22.0, 9.5.

Stage 4: Thermolysis

A few grams of 1,8-[N,N',O,O'-tetrakis(trimethylsilyl)-carbamato]-octane (6) were filled into the still pot of the kugelrohr distillation apparatus under inert conditions. The still pot and the middle pot were put into the heating chamber (tubular furnace), while cooling the outer pot in the water bath. The carbamate was heated to 170° C. for 1 hour, to 200° C. for 1 hour, and to 250° C. for 30 min, while continuously rotating the kugelrohr distillation apparatus with 30 rpm. At the end of the heating phase accumulation of colorless liquid in the outer pot was observed, while in the still pot a yellow, polymer-like layer was formed. After thermolysis has taken place the individual pots of the kugelrohr distillation apparatus were separately analyzed by NMR spectroscopy. The presence of the diisocyanate was clearly detected by means of NMR and IR spectroscopy.

The $^{13}$C-NMR spectrum of the outer pot in addition to hexamethyldisiloxane ($^{13}$C: δ=2.0 ppm, $^{29}$Si: δ=7.1 ppm) showed the diisocyanate at a shift of 120.5 ppm. The associated band in the IR-ATR spectrum is at 2253 $cm^{-1}$. Comparing with a commercial sample of 1,8-diisocyanatooctane provided exact matches.

Example 4

Synthesis of isopentyl-isocyanate (21)

i-Pentyl-isocyanate (compound 21) was prepared according to the method shown in scheme 11. i-Pentyl-isocyanate is another example of an aliphatic mono-isocyanate. With respect to scheme 11, in example 4 $R^1$ is i-pentyl, $R^2$ and $R^3$ at each occurrence are methyl, $X^1$ is chlorine and X is triflate. The term “i-pentyl” or “isopentyl” is meant to be a group of formula $(H_3C)_2CH—CH_2—CH_2—$.

N,O-Bis(trimethylsilyl)-N,i-pentyl-carbamate (22) is a compound of general formula IV-A in which $R^1$ is i-pentyl. N,O-bis(trimethylsilyl)-N,i-pentyl-carbamate (22) has the following formula:

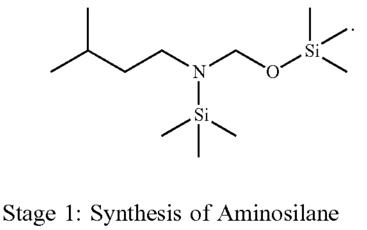

Stage 1: Synthesis of Aminosilane

First, 5.65 g (64.81 mmol) of i-pentylamine together with 9.81 g (96.99 mmol) of triethylamine were provided in 150 ml of diethyl ether. 9.81 g (90.32 mmol) of trimethyl chlorosilane were added under stirring in the ice bath via a dropping funnel. When adding the silane dropwise formation of a white solid was observed in addition to the development of white smoke. Subsequently, the mixture was heated to room temperature and stirred for 96 hours. The solid was separated by filtration and the solvent was removed under reduced pressure. The aminosilane N-trimethylsilyl-i-pentylamine was obtained as a colorless liquid in a yield of 88% (9.12 g, 57.25 mmol). Purity of the product was confirmed by NMR spectroscopy.

$^1$H-NMR (500 MHz, $CDCl_3$, δ [ppm]): 2.69 (t, J=7.4 Hz, 2H), 1.60 (dq, J=13.4, 6.7 Hz, 1H), 1.29-1.21 (m, 2H), 0.85 (d, J=6.7 Hz, 6H), 0.24 (s, 1H, NH), 0.00 (s, 9H, $SiMe_3$). $^{13}$C-NMR (101 MHz, $CDCl_3$, δ [ppm]): 44.2 ($CH_2$), 39.9 ($CH_2$), 25.5 (CH), 22.6 ($CH_3$), −0.1 ($SiMe_3$). $^{29}$Si-NMR (79 MHz, $CDCl_3$, δ [ppm]): 3.0.

Stage 2: $CO_2$ Insertion 7.99 g (50.11 mmol) of N-trimethylsilyl-1-pentylamine were mixed with 10 ml of dry THE and transferred to an autoclave under inert conditions. The autoclave was pressurized with a $CO_2$ pressure of 8 bar. The reaction was carried out under constant stirring for a period of 3 hours. After having relieved the pressure and inert transferred the reaction mixture to a Schlenk vessel the solvent was removed by cold distillation and the insertion product was recovered as a clear, colorless liquid. 9.55 g (46.98 mmol) of N,i-pentyl-O-trimethylsilyl-carbamate were obtained. This corresponds to a yield of 94%. The identity and purity of the target compound were confirmed by NMR spectroscopy.

$^1$H-NMR (500 MHz, $CDCl_3$, δ [ppm]): 5.19 (t, J=6.1 Hz, 1H, NH), 2.92-2.81 (m, 2H), 1.36 (dp, J=13.3, 6.7 Hz, 1H), 1.17-1.06 (m, 2H), 0.65 (d, J=6.7 Hz, 6H), 0.00 (s, 9H, SiMe3). $^{13}$C-NMR (101 MHz, $CDCl_3$, δ [ppm]): 155.1 (CO), 40.1 ($CH_2$), 39.0 ($CH_2$), 25.5 (CH), 22.2 ($CH_3$), −0.3 (SiMe3). $^{29}$Si-NMR (79 MHz, $CDCl_3$, δ [ppm]): 21.8.

Stage 3: Silylation 9.55 g (46.98 mmol) of N,i-pentyl-O-trimethylsilyl-carbamate were dissolved in 90 ml of n-pentane together with 5.07 g (50.06 mmol) of triethylamine and stirred in the ice bath. 11.02 g (49.59 mmol) of trimethylsilyltriflate were added dropwise via a dropping funnel thereby formation of a white second phase at the bottom of the Schlenk flask was observed. Subsequently, the mixture was stirred over night at room temperature. The 2$^{nd}$ phase formed was congealed in the dry ice/isopropanol cold mixture—and the supernatant solution was decanted off. The solvent was removed by cold distillation. In this way, 8.38 g (30.40 mmol, yield 65%) of N,O-bis(trimethylsilyl)-N,i-pentyl-carbamate (22) were obtained as a pale yellow liquid. The identity of the target product was confirmed by NMR spectroscopy.

$^1$H-NMR (500 MHz, $CDCl_3$, δ [ppm]): 2.93-2.80 (m, 2H), 1.31 (dh, J=13.3, 6.7 Hz, 1H), 1.13 (ddd, J=11.7, 7.6, 5.9 Hz, 2H), 0.67 (d, J=6.7 Hz, 6H), 0.06 (s, 9H, $SiMe_3$), 0.00 (s, 9H, $SiMe_3$). $^{13}$C-NMR (101 MHz, $CDCl_3$, δ [ppm]): 157.3 (CO), 43.0 ($CH_2$), 39.6 ($CH_2$), 26.2 (CH), 22.4 ($CH_3$), 0.5 ($SiMe_3$), −0.3 ($SiMe_3$). $^{29}$Si-NMR (79 MHz, $CDCl_3$, δ [ppm]): 21.9 (Si—O), 9.5 (Si—N).

Stage 4: Thermolysis 1.38 g (4.99 mmol) of N,O-bis(trimethylsilyl)-N,i-pentyl-carbamate (22) were filled into the still pot of the kugelrohr distillation apparatus under inert conditions. The still pot and the middle pot were put into the heating chamber (tubular furnace) and the apparatus was adjusted to an inclination of 45°. The carbamate was heated to 250° C. for 1 hour and to 300° C. for another 30 min at continuous rotation at 30 rpm. Subsequently, the apparatus was brought into a horizontal position and heated to 300° C. for 30 min again. In the outer and middle pots a colorless liquid has accumulated. At the end of the reaction time the still pot was almost empty. Subsequently, the pots were cooled to room temperature and inert transferred to Schlenk vessels. Analysis of the colorless liquid of the outer pot was carried out by means of NMR spectroscopy. The $^{29}$Si-NMR spectrum only indicates the presence of hexamethyldisiloxane (7.1 ppm). The carbamate used is completely decomposed. These results are confirmed by the $^{13}$C-NMR spectrum (hexamethyldisiloxane at 1.7 ppm). Moreover, a signal at 122.2 ppm is found in the $^{13}$C-NMR spectrum which can clearly be assigned to the isopentyl-isocyanate (other associated signals: 41.0, 40.1, 25.2, 21.9 ppm). Assignment was additionally confirmed by IR spectroscopy. The characteristic vibration of the carbonyl group of the carbamate at about 1690 $cm^{-1}$ has completely disappeared, while the intensive isocyanate band is found at 2270 $cm^{-1}$. The bands at 1252, 1053, 841 $cm^{-1}$ can be assigned to the hexamethyldisiloxane.

Example 5

Synthesis of benzylisocyanate (23)

Benzylisocyanate (compound 23) was prepared according to the method shown in scheme 11. Benzylisocyanate is another example of an aliphatic monoisocyanate. With respect to scheme 11, in example 5 $R^1$ is benzyl, $R^2$ and $R^3$ at each occurrence are methyl, $X^1$ is chlorine and X is triflate. The term "benzyl" is meant to be a group of formula $H_5C_6$—$CH_2$—.

Stage 1: Synthesis of Aminosilane

First, 5.03 g (46.90 mmol) of benzylamine together with 4.91 g (48.55 mmol) of triethylamine were provided in 160 ml of diethyl ether. 5.17 g (47.56 mmol) of trimethyl chlorosilane were added via a dropping funnel under stirring in the ice bath whereby formation of a white solid and development of white smoke was observed. Subsequently, the mixture was heated to room temperature and stirred overnight. The solid was separated by filtration and the solvent was removed by cold distillation. The aminosilane N-trimethylsilyl-benzylamine was obtained as a colorless liquid in a yield of 89% (7.45 g, 41.52 mmol). Purity of the product was confirmed by NMR spectroscopy.

$^1$H-NMR (500 MHz, $CDCl_3$, δ [ppm]): 7.15 (m, 4H), 7.05 (m, 1H), 3.77 (d, J=8.0 Hz, 2H), 0.55 (s, 1H, NH), 0.00 (s, 9H, $SiMe_3$). $^{13}$C-NMR (101 MHz, $CDCl_3$, 6 [ppm]): 144.2 (C), 128.1 (CH), 126.8 (CH), 126.3 (CH), 45.6 (CH2), 0.0 ($SiMe_3$). $^{29}$i-NMR (79 MHz, $CDCl_3$, δ [ppm]): 3.9.

Stage 2: $CO_2$ Insertion 6.78 g (37.81 mmol) of N-trimethylsilyl-benzylamine were mixed with 20 ml of dry THF, transferred to an autoclave under inert conditions and pressurized with a $CO_2$ pressure of 8 bar within one hour. After having relieved the pressure and inert transferred the reaction mixture to a Schlenk vessel the solvent was removed by cold distillation and the insertion product was recovered as a colorless, viscous liquid with a yield of 94% (7.90 g, 35.37 mmol). After some days of storage at room temperature formation of colorless crystals was observed. The identity and purity of the target compound was confirmed by NMR spectroscopy.

$^1$H-NMR (500 MHz, $CDCl_3$, δ [ppm]): 7.14 (m, 5H), 6.17 (s, 1H, NH), 4.15 (d, J=6.2 Hz, 2H, $CH_2$), 0.23 (s, 9H, $SiMe_3$). $^{13}$C-NMR (101 MHz, $CDCl_3$, δ [ppm]): 155.0 (CO), 128.6 (C), 127.8 (CH), 126.8 (CH), 126.5 (CH), 44.2 (CH2), −0.5 ($SiMe_3$). $^{29}$i-NMR (79 MHz, $CDCl_3$, δ [ppm]): 23.2. Elemental analysis: calculated N, 6.27%, C, 59.16%, H, 7.67%, measured N, 6.81%, C, 59.02%, H, 7.408%

Stage 3: Silylation 30.33 g (135.80 mmol) of N-benzyl-O-trimethylsilyl-carbamate were dissolved in 100 ml of diethyl ether together with 14.48 g (143.07 mmol) of triethylamine and stirred in the ice bath. 32.62 g (146.76 mmol) of trimethylsilyltriflate were added dropwise via a dropping funnel thereby formation of a white second phase was observed at the bottom of the Schlenk flask. Subsequently, the mixture was stirred at room temperature overnight, before the 2$^{nd}$ phase formed was congealed in the dry ice/isopropanol cold mixture and the supernatant solution was decanted off. The solvent was removed from the reaction solution by cold distillation and provided the target product, N,O-bis(trimethylsilyl)-N-benzyl-carbamate (5), as an intensively yellow, slightly viscous liquid (37.58 g, 127.17 mmol, 94% yield). The identity of the target product was confirmed by NMR spectroscopy.

$^1$H-NMR (500 MHz, $CDCl_3$, δ [ppm]): 7.18 (m, 5H), 4.41 (s, 2H, $CH_2$), 0.33 (s, 9H, $SiMe_3$), 0.19 (s, 9H, $SiMe_3$). $^{13}$C-NMR (101 MHz, $CDCl_3$, δ [ppm]): 158.2 (CO), 140.4 (C), 128.4 (CH), 126.6 (CH), 126.4 (CH), 48.1 ($CH_2$), 0.8 (SiMe3), 0.0 (SiMe3). $^{29}$Si-NMR (79 MHz, $CDCl_3$, δ [ppm]): 22.6 (O—Si), 10.9 (N—Si).

Stage 4: Thermolysis 3.13 g (4.50 mmol) of N,O-bis(trimethylsilyl)-N-benzyl-carbamate (5) were filled into the still pot of the kugelrohr distillation apparatus under inert conditions. The still pot and the middle pot were put into the heating chamber (tubular furnace) and the apparatus was adjusted to an inclination of 45°. The carbamate was heated to 200° C. and 250° C. for 30 minutes each, to 300° C. for 10 minutes, and to 250° C. for another 90 minutes with continuous rotation at 20 rpm. Pressure compensation was ensured via an oil trap. 50 Minutes after the start of heating the apparatus was placed in a horizontal position. A colorless liquid (1.82 g) has accumulated in the outer pot and a yellow liquid (0.38 g) in the middle pot from 250° C. At the end of the reaction time a small amount of a highly viscous, dark brown residue (0.64 g) was contained in the still pot. Subsequently, the pots were cooled to room temperature and inert transferred to Schlenk vessels with $CDCl_3$ as the solvent. Analysis of the fractions was by NMR spectroscopy.

Outer pot: The $^{29}$Si-NMR spectrum only indicated the presence of hexamethyldisiloxane (7.3 ppm). The carbamate used was completely decomposed.

These results were confirmed by the $^{13}$C-NMR spectrum (hexamethyldisiloxane at 1.7 ppm). Moreover, signals were found in the $^{13}$C-NMR spectrum which can clearly be assigned to the benzylisocyanate by comparison with a commercially available sample (137.0, 128.7, 127.8, 126.6, 123.7, 46.4 ppm). Both the middle fraction and the residue showed a variety of signals in the $^{29}$Si and $^{13}$C-NMR spectra. An assignment could not be made. Analysis by gas chromatography provided further information on the composition of the outer fraction: retention time (RT) 1.565 min-16.95%-$CDCl_3$; RT 1.771 min-0.68%-$Me_3$Si-isocyanate (wherein Me designates a methyl group); RT 2.043 min-64.85%-hexamethyldisiloxane (HMDSO); RT 2.554 min-3.67%-toluene; RT 6.447 min-9.48%-benzylisocyanate (23); RT 10.765 min-0.81%-N,O-bis(trimethylsilyl)-N-benzyl-carbamate (5).

In another experiment, 8.38 g (28.36 mmol) of N,O-bis (trimethylsilyl)-N-benzyl-carbamate (5) were directly heated to 300° C. for 2.5 hours in the kugelrohr distillation apparatus at 30 rpm under standard pressure. For the first hour the apparatus was adjusted to an inclination of 45°. After expiration of the reaction time a colorless liquid with white flakes has accumulated in the outer pot (1.74 g), while the middle pot was almost empty (0.22 g) and a highly viscous, deep brown residue (2.47 g) has formed in the still pot. All fractions were analyzed by NMR spectroscopy. Again, a variety of signals has appeared in the $^{29}$Si and $^{13}$C-NMR spectra of the middle pot and the residue which could not further be assigned. The outer pot in addition to HMDSO (7.3 ppm) also contained trimethylsilylisocyanate (4.2 ppm) as the silicon-containing component in the $^{29}$Si-NMR spectrum. This was confirmed in the $^{13}$C-NMR spectrum: HMDSO (1.9 ppm), $Me_3$SiNCO (0.9, 124.0 ppm). In addition, it was noted that the $CH_2$ bridge of the benzyl group at about 46 ppm was not present, but instead an intensive signal appeared at 21.5 ppm. Formation of toluene was identified together with the signals in the aromatic shift area (137.9, 129.2, 128.4, 125.5, 21.5 ppm).

Example 6

Synthesis of Allylisocyanate (24)

Allylisocyanate (compound 24) was prepared according to the method shown in scheme 11. Allylisocyanate is another example of an aliphatic monoisocyanate. With respect to scheme 11, in example 6 $R^1$ is allyl, $R^2$ and $R^3$ at each occurrence are methyl, $X^1$ is chlorine and X is triflate. The term "allyl" is meant to be a group of formula $H_2C{=}CH{-}CH_2{-}$.

N,O-Bis(trimethylsilyl)-N-allyl-carbamate (25) is a compound of general formula IV-A in which $R^1$ is allyl. N,O-Bis(trimethylsilyl)-N-allyl-carbamate (25) has the following formula:

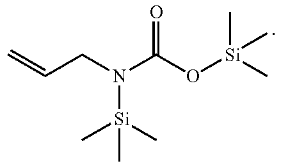

Stage 1: Synthesis of Aminosilane

To a mixture of 5.07 g (88.75 mmol) of allylamine and 8.86 g (87.53 mmol) of triethylamine in 100 ml dry n-pentane 9.73 g (89.59 mmol) of trimethylchlorosilane were added dropwise under stirring and cooling with an ice bath. A white precipitate was formed which was separated by filtration after 2 days of stirring at room temperature. The solvent was separated by cold distillation and the success of the synthesis was examined by NMR spectroscopy. In addition to the desired N-trimethylsilyl-allylamine (26) the associated silazane (N,N-bis(trimethylsilyl)-allylamine (27) was formed.

$^1$H-NMR (500 MHz, $CDCl_3$, δ [ppm]): 5.82-5.59 (m, 1H), 4.2 (dd, J=17.0, 1.8 Hz, 2H), 4.76 (dd, J=10.1, 1.5 Hz, 1H), 3.26 (dt, J=4.4, 2.0 Hz, OH), 3.14 (d, J=5.3 Hz, 7H), −0.09 (s, 2H), −0.15 (s, 9H, $SiMe_3$). $^{13}$C-NMR (101 MHz, $CDCl_3$, δ [ppm]): 141.2 (27)/140.9 (26) (CH), 113.3 (27)/112.8 (26) (CH2), 47.4 (27)/44.6 (26) ($CH_2$), 0.0 ($SiMe_3$). $^{29}$Si-NMR (79 MHz, $CDCl_3$, δ [ppm]): 4.1 (26), 6.5 (27).

Stage 2: $CO_2$ Insertion 7.65 g (59.18 mmol) of N-trimethylsilyl-allylamine (commercially purchased) were mixed with 20 ml of dry THE and transferred to an autoclave under inert conditions. $CO_2$ insertion reaction was performed with a $CO_2$ pressure of 8 bar with constant stirring for a period of 43.5 hours. After having relieved the pressure and inert transferred the reaction mixture with 5 ml of THE to a Schlenk vessel the solvent was removed by cold distillation and the insertion product was recovered as an intensively yellow, slightly viscous liquid. In this way, 9.55 g (55.10 mmol, yield 93%) of N-allyl-O-trimethylsilyl-carbamate were obtained. The identity and purity of the target compound were confirmed by NMR spectroscopy.

$^1$H-NMR (500 MHz, $CDCl_3$, δ [ppm]): 5.70-5.45 (m, 1H), 5.29 (s, 1H, NH), 4.93 (dd, J=17.2, 1.6 Hz, 1H), 4.84 (dd, J=10.3, 1.5 Hz, 1H), 3.50 (t, J=5.7 Hz, 2H), 0.04 (s, 9H, SiMe3). $^{13}$C-NMR (101 MHz, $CDCl_3$, δ [ppm]): 155.6 (CO), 135.2 (CH), 115.7 ($CH_2$), 43.7 ($CH_2$), 0.3 (SiMe3). $^{29}$Si-NMR (79 MHz, $CDCl_3$, δ [ppm]): 22.3.

Stage 3: Silylation 8.43 g (48.62 mmol) of N-allyl-O-trimethylsilyl-carbamate were dissolved in 100 ml of n-pentane together with 5.28 g (52.14 mmol) of triethylamine and stirred in an ice bath. 11.37 g (51.15 mmol) of trimethylsilyltriflate were added dropwise thereby formation of an intensively orange, second phase was observed at the bottom of the Schlenk flask. Subsequently, the mixture was stirred overnight at room temperature. The $2^{nd}$ phase obtained was congealed in the dry ice/isopropanol cold mixture and the supernatant solution was decanted off. After having removed the solvent by cold distillation 10.24 g (41.70 mmol, yield 86%) of N,O-bis(trimethylsilyl)-N-allyl-carbamate (25) were obtained as an orange liquid. The identity of the target product was confirmed by NMR spectroscopy.

$^1$H-NMR (500 MHz, $CDCl_3$, δ [ppm]): 5.67-5.53 (m, 1H), 4.88 (d, J=1.8 Hz, 2H), 4.86-4.80 (m, 2H), 3.56 (d, J=5.1 Hz, 2H), 0.10 (s, 9H, $SiMe_3$), 0.04 (s, 9H, $SiMe_3$). $^{13}$C-NMR (101 MHz, $CDCl_3$, δ [ppm]): 157.4 (CO), 136.1 (CH), 114.3 ($CH_2$), 46.7 ($CH_2$), 0.6 ($SiMe_3$), −0.1 ($SiMe_3$). $^{29}$Si-NMR (79 MHz, $CDCl_3$, δ [ppm]): 22.4 (Si—O), 10.5 (Si—N).

Stage 4: Thermolysis 1.09 g (4.43 mmol) of N,O-bis(trimethylsilyl)-N-allyl-carbamate (25) were filled into the still pot of the kugelrohr distillation apparatus under inert conditions and put into the heating chamber (tubular furnace) together with the middle pot. The apparatus was adjusted to an inclination of 45°. The carbamate was heated to 250° C. for 1 hour and to 300° C. for another 30 min with continuous rotation at 30 rpm under standard pressure. The apparatus was placed in the horizontal position one hour after starting heating. In the outer pot a colorless liquid has accumulated. While the middle pot at the end of the reaction time was almost empty, a black film has formed on the glass wall in the still pot. Subsequently, the pots were cooled to room temperature and the outer fraction was inert transferred to Schlenk vessels, before the composition was analyzed NMR spectroscopy. The $^{29}$Si-NMR spectrum only indicated the presence of hexamethyldisiloxane (7.2 ppm), while the carbamate used was completely decomposed. These results were confirmed by the $^{13}$C-NMR spectrum (hexamethyldisiloxane at 2.0 ppm). The other signals in the $^{13}$C-NMR spectrum indicated an exact match with a sample of commercially available allylisocyanate. The signals are located as follows: 133.3, 123.9, 116.1, 39.7 ppm. The assignment was additionally confirmed by the characteristic vibration of the isocyanate group at 2262 $cm^{-1}$ in the IR spectrum. Determination of contents by gas chromatography resulted in a composition of 66.05% of hexamethyldisiloxane and 28.38% of allylisocyanate.

The invention claimed is:

1. A method for the preparation of isocyanates, comprising:

(i) converting a first organosilicon compound having at least one silicon atom $Si^1$ and a unit of formula G-I bound thereto (formula G-I)

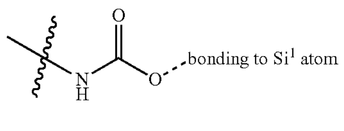

to a third organosilicon compound having a unit of formula G-II (formula G-II)

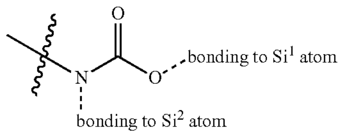

by silylation of the NH group of the unit of formula G-I with a second organosilicon compound having one silicon atom $Si^2$; and (ii) reacting the third organosilicon compound by thermolysis, whereby the unit of formula G-II is converted to an isocyanate group.

2. The method according to claim 1, wherein the first organosilicon compound is a compound of formula II (formula II)

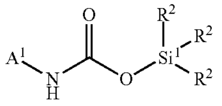

wherein $A^1$ is $R^1$ or a group of formula G-III:

(formula G-III)

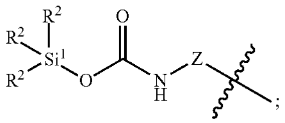

$R^1$ is a substituted or unsubstituted, aliphatic or aromatic group;

$R^2$ at each occurrence each independently is selected from the group consisting of hydrogen, a substituted or unsubstituted alkyl group with 1 to 12 carbon atoms and a substituted or unsubstituted aryl group, with the proviso that at least one residue $R^2$ which is not hydrogen is bound to each silicon atom $Si^1$; and Z is a substituted or unsubstituted, aliphatic or aromatic group;

the second organosilicon compound is a compound of formula III (formula III)

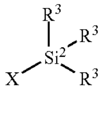

wherein

X is selected from the group consisting of a halogen, —CN, —OCN, —SCN, —$N_3$, a sulphonate, a carbamate, —O—$R^4$, —$NR^7R^8$ or an N-heterocycle;

$R^3$ at each occurrence each independently is selected from the group consisting of hydrogen, a substituted or unsubstituted alkyl group with 1 to 12 carbon atoms and a substituted or unsubstituted aryl group, with the proviso that at least one residue R3which is not hydrogen is bound to each silicon atom $Si^2$;

$R^4$ is —C(O)$R^9$ or a group of formula G-VI (formula G-VI)

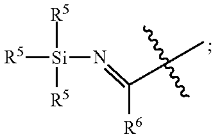

$R^5$ at each occurrence each independently is a substituted or unsubstituted alkyl group with 1 to 12 carbon atoms;

$R^6$ is a substituted or unsubstituted alkyl group with 1 to 12 carbon atoms;

$R^7$ and $R^8$ each independently are —C(O)$R^9$ or a substituted or unsubstituted alkyl group with 1 to 12 carbon atoms; and $R^9$ is a substituted or unsubstituted alkyl group with 1 to 12 carbon atoms;

and the third organosilicon compound is a compound of formula IV (formula IV)

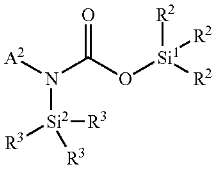

wherein $A^2$ is $R^1$ or a group of formula G-IV:

(formula G-IV)

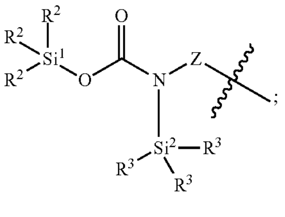

$R^2$ at each occurrence and Z have the meanings given in connection with the compound of formula II; and $R^3$ at each occurrence has the meanings given in connection with the compound of formula III;

wherein the compound of formula II is silylated with the compound of formula III to produce the compound of formula IV and the compound of formula IV is reacted by thermolysis to produce an isocyanate compound of formula I $A^3$-N═C═O (formula I), wherein $A^3$ is $R^1$ or a group of formula G-V:

(formula G-V)

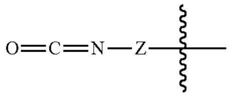

$R^1$ and Z have the meanings given in connection with the compound of formula II.

3. The method according to claim 2, wherein $R^1$ in the compounds of formula I, II and IV is selected from the group consisting of a substituted or unsubstituted alkyl group with 1 to 18 carbon atoms, a substituted or unsubstituted heteroalkyl group with 1 to 18 carbon atoms, a substituted or unsubstituted alkenyl group with 2 to 18 carbon atoms, a substituted or unsubstituted alkynyl group with 2 to 18 carbon atoms, a substituted or unsubstituted aryl group and a substituted or unsubstituted heteroaryl group.

4. The method according to claim 2, wherein $R^1$ in the compounds of formula I, II and IV is selected from the group consisting of methyl, ethyl, propyl, butyl, pentyl, hexyl, octyl, and phenyl.

5. The method according to claim 2, wherein Z in the compounds of formula I, II and IV is selected from the group consisting of a substituted or unsubstituted alkylene group with 1 to 12 carbon atoms, a substituted or unsubstituted phenylene group, and a substituted or unsubstituted phenylene-bisalkylene group in which each alkylene group at each occurrence each independently is an alkylene group with 1 to 12 carbon atoms.

6. The method according to claim 2, wherein X in the compound of formula III is selected from the group consisting of chlorine, a toluene sulphonic acid ester group, a methyl sulphonic acid ester group, and a trifluoromethyl sulphonic acid ester group.

7. A compound according to claim 2, wherein $R^3$ at each occurrence in the compounds of formula III and IV each independently is a substituted or unsubstituted alkyl group with 1 to 6 carbon atoms or a substituted or unsubstituted phenyl group.

8. The compound according to claim 2, wherein all of $R^2$ in the compounds of II and IV each are methyl groups and/or all of $R^3$ in the compounds of general formula III and IV each are a methyl group.

9. The method according to claim 2, wherein the silylation is carried out at a temperature of 0 to 50° C.

10. The method according to claim 2, wherein the silylation is carried out in a non-polar organic solvent in the presence of an auxiliary base.

11. The method according to claim 2, wherein the thermolysis is carried out at a temperature of 150 to 400° C.

12. The method according to claim 2, wherein the thermolysis is carried out using a temperature profile comprising two or more temperature stages, wherein each temperature stage is applied for a given time period and each of the applied temperature stages is above the previously applied temperature range by 20 to 80° C.

13. The method according to claim 12, wherein the given period of time is between 1 min and 2 hrs.

14. The method according to claim 2, wherein the thermolysis is carried out in the presence of an inert gas.

15. A method for the preparation of an isocyanate compound of formula I $A^3$-N═C═O (formula I), wherein $A^3$ is $R^1$ or a group of formula G-V:

(formula G-V)

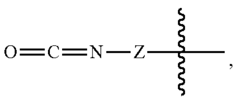

$R^1$ and Z have the meanings given in connection with the compound of formula II, said method comprising silylating a compound of formula II (formula II)

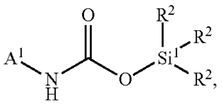

wherein $A^1$ is $R^1$ or a group of formula G-III:

(formula G-III)

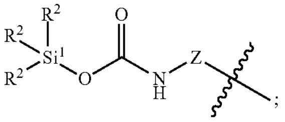

$R^1$ is a substituted or unsubstituted, aliphatic or aromatic group;

$R^2$ at each occurrence each independently is selected from the group consisting of hydrogen, a substituted or unsubstituted alkyl group with 1 to 12 carbon atoms and a substituted or unsubstituted aryl group, with the proviso that at least one residue $R^2$ which is not hydrogen is bound to each silicon atom $Si^1$;

Z is a substituted or unsubstituted, aliphatic or aromatic group; and reacting the silylated compound of formula II by thermolysis, whereby the silylated compound of formula II is converted to an isocyanate group.

* * * * *